United States Patent
Balasubramanian et al.

(10) Patent No.: US 10,993,813 B2
(45) Date of Patent: *May 4, 2021

(54) PROSTHETIC SPINAL DISC REPLACEMENT AND METHODS THEREOF

(71) Applicant: GLOBUS MEDICAL, INC., Audubon, PA (US)

(72) Inventors: Anand Balasubramanian, Collegeville, PA (US); Edward Dwyer, Lehighton, PA (US); David Peretz, Wynnewood, PA (US); David W. Ankney, Murraysville, PA (US); William Rhoda, Media, PA (US); David C. Paul, Phoenixville, PA (US); Christopher Angelucci, Schwenksville, PA (US)

(73) Assignee: Globus Medical, Inc., Audubon, PA (US)

( * ) Notice: Subject to any disclaimer, the term of this patent is extended or adjusted under 35 U.S.C. 154(b) by 74 days.

This patent is subject to a terminal disclaimer.

(21) Appl. No.: 16/401,333

(22) Filed: May 2, 2019

(65) Prior Publication Data
US 2019/0254834 A1    Aug. 22, 2019

Related U.S. Application Data

(63) Continuation of application No. 15/811,777, filed on Nov. 14, 2017, now Pat. No. 10,314,716, which is a
(Continued)

(51) Int. Cl.
*A61F 2/44* (2006.01)
*A61B 17/16* (2006.01)
(Continued)

(52) U.S. Cl.
CPC .......... *A61F 2/442* (2013.01); *A61B 17/1671* (2013.01); *A61B 17/1757* (2013.01); *A61F 2/44* (2013.01); *A61F 2/4425* (2013.01); *A61F 2/4611* (2013.01); *A61F 2/4684* (2013.01); *A61B 17/1604* (2013.01); *A61B 17/1735* (2013.01); *A61B 2017/0046* (2013.01); *A61B 2017/0256* (2013.01); *A61F 2002/302* (2013.01); *A61F 2002/30014* (2013.01);
(Continued)

(58) Field of Classification Search
CPC .......... A61F 2/44; A61F 2/442; A61F 2/4425; A61F 2002/443
See application file for complete search history.

(56) References Cited

U.S. PATENT DOCUMENTS 7,326,250 B2 * 2/2008 Beaurain ............... A61F 2/4425
                                                            623/17.14
8,167,948 B2   5/2012 Paul et al.
(Continued)

FOREIGN PATENT DOCUMENTS

JP         2008-522737 A     7/2008

*Primary Examiner* — Nicholas W Woodall

(57) ABSTRACT

The present invention relates generally to a prosthetic spinal disc for replacing a damaged disc between two vertebrae of a spine and methods for inserting said discs. The intervertebral prosthetic discs are provided with connections for facilitating implantation and removal and features which enhance primary and secondary stability over time.

20 Claims, 42 Drawing Sheets

Related U.S. Application Data continuation of application No. 14/303,220, filed on Jun. 12, 2014, now Pat. No. 9,844,442, which is a continuation-in-part of application No. 13/889,876, filed on May 8, 2013, now Pat. No. 9,125,751, which is a continuation of application No. 11/366,390, filed on Mar. 3, 2006, now Pat. No. 7,811,329, which is a continuation-in-part of application No. 11/318,438, filed on Dec. 28, 2005, now Pat. No. 7,713,304, which is a continuation-in-part of application No. 11/246,149, filed on Oct. 11, 2005, now Pat. No. 8,167,948, which is a continuation-in-part of application No. 10/909,210, filed on Jul. 30, 2004, now Pat. No. 7,641,666, which is a continuation-in-part of application No. 10/827,642, filed on Apr. 20, 2004, now Pat. No. 7,621,956.

(60) Provisional application No. 60/491,271, filed on Jul. 31, 2003.

(51) Int. Cl.
 A61B 17/17 (2006.01)
 A61F 2/46 (2006.01)
 A61F 2/30 (2006.01)
 A61B 17/00 (2006.01)
 A61B 17/02 (2006.01)

(52) U.S. Cl.
 CPC ............ *A61F 2002/3092* (2013.01); *A61F 2002/30113* (2013.01); *A61F 2002/30125* (2013.01); *A61F 2002/30153* (2013.01); *A61F 2002/30166* (2013.01); *A61F 2002/30224* (2013.01); *A61F 2002/30365* (2013.01); *A61F 2002/30387* (2013.01); *A61F 2002/30433* (2013.01); *A61F 2002/30451* (2013.01); *A61F 2002/30471* (2013.01); *A61F 2002/30517* (2013.01); *A61F 2002/30545* (2013.01); *A61F 2002/30563* (2013.01); *A61F 2002/30568* (2013.01); *A61F 2002/30571* (2013.01); *A61F 2002/30579* (2013.01); *A61F 2002/30594* (2013.01); *A61F 2002/30601* (2013.01); *A61F 2002/30604* (2013.01); *A61F 2002/30616* (2013.01); *A61F 2002/30649* (2013.01); *A61F 2002/30662* (2013.01); *A61F 2002/30769* (2013.01); *A61F 2002/30772* (2013.01); *A61F 2002/30841* (2013.01); *A61F 2002/30878* (2013.01); *A61F 2002/30884* (2013.01); *A61F 2002/30899* (2013.01); *A61F 2002/30935* (2013.01); *A61F 2002/443* (2013.01); *A61F 2002/448* (2013.01); *A61F 2002/4627* (2013.01); *A61F 2002/4629* (2013.01); *A61F 2002/4681* (2013.01); *A61F 2310/00407* (2013.01); *A61F 2310/00796* (2013.01)

(56) References Cited

U.S. PATENT DOCUMENTS

| | | | |
|---|---|---|---|
| 8,425,603 B2* | 4/2013 | Reichen | A61F 2/4611 623/17.11 |
| 2004/0117022 A1* | 6/2004 | Marnay | A61F 2/4611 623/17.16 |
| 2004/0143332 A1* | 7/2004 | Krueger | A61B 17/1604 623/17.14 |
| 2005/0187631 A1* | 8/2005 | Van Hoeck | A61F 2/4425 623/17.13 |
| 2006/0149273 A1 | 7/2006 | Ross et al. | |
| 2007/0055378 A1* | 3/2007 | Ankney | A61F 2/4425 623/17.15 |
| 2014/0052256 A1 | 2/2014 | Ankney et al. | |

* cited by examiner

PROSTHETIC SPINAL DISC REPLACEMENT AND METHODS THEREOF

CROSS REFERENCE TO RELATED APPLICATIONS

This application is a continuation of U.S. patent application Ser. No. 18/811,777 filed on Nov. 14, 2017 which is a continuation of U.S. Ser. No. 14/303,220, filed on Jun. 12, 2014 (published as U.S. Patent Publication No. 2014-0296985), which is a continuation-in-part of U.S. Ser. No. 13/889,876, filed May 8, 2013, now U.S. Pat. No. 9,125,751, which is a continuation of U.S. Ser. No. 11/366,390, filed Mar. 3, 2006, now U.S. Pat. No. 7,811,329, which is a continuation-in-part of U.S. Ser. No. 11/318,438, filed Dec. 28, 2005, now U.S. Pat. No. 7,713,304, which is a continuation-in-part of U.S. Ser. No. 11/246,149, filed Oct. 11, 2005, now U.S. Pat. No. 8,167,948, which claims priority to U.S. Ser. No. 10/909,210, filed Jul. 30, 2004, now U.S. Pat. No. 7,641,666, U.S. Ser. No. 10/827,642, filed Apr. 20, 2004, now U.S. Pat. No. 7,621,956, and U.S. Provisional Application 60/491,271, filed Jul. 31, 2003. Each of these references is incorporated herein by reference in their entireties.

FIELD OF THE INVENTION

The disclosure relates to a prosthetic spinal disc for fully or partially replacing a damaged disc between two vertebrae of a spine.

BACKGROUND OF THE INVENTION

The vertebrate spine is the axis of the skeleton on which a substantial portion of the weight of the body is supported. In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints and allow known degrees of flexion, extension, lateral bending, and axial rotation.

The typical vertebra has a thick anterior bone mass called the vertebral body, with a neural (vertebral) arch that arises from the posterior surface of the vertebral body. The centers of adjacent vertebrae are supported by intervertebral discs. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch which extends posteriorly and acts to protect the spinal cord's posterior side is known as the lamina. Projecting from the posterior region of the neural arch is the spinous process.

The vertebrae also contain four articular processes that extend from the posterior region of the vertebra. There are two articular processes on the left side of the vertebra and two articular processes on the right side of the vertebra. Two of the four processes (one on the left and one on the right) extend upwards from the top of the laminae and are referred to as the superior articular processes. The other two processes (again one on the left and one on the right) extend downwards from the bottom of the laminae and are referred as the inferior articular processes. In a healthy spine the left and right superior articular processes of a vertebra form synovial joints with the left and right inferior articular processes of the superior adjacent vertebra. These joints are also referred to as facet joints. The facet joints are synovial joints as the joints are encapsulated with connective tissue and lubricated by synovial fluid. The joint faces are also covered with smooth cartilage, which acts to reduce friction and absorb shock.

The intervertebral disc primarily serves as a mechanical cushion permitting controlled motion between vertebral segments of the axial skeleton. The normal disc is a unique, mixed structure, comprised of three component tissues: the nucleus pulpous ("nucleus")*the annulus fibrosus ("annulus") and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc: In other words, a transitional zone is created by the end plates between the malleable disc and the bony vertebrae.

The annulus of the disc is a tough, outer fibrous ring which binds together adjacent vertebrae. The fibrous portion, which is much like a laminated automobile tire, measures about 10 to 15 millimeters in height and about IS to 20 millimeters in thickness. The fibers of the annulus consist of fifteen to twenty overlapping multiple plies, and are inserted into the superior and inferior vertebral bodies at roughly a 40 degree angle in both directions. This configuration particularly resists torsion, as about half of the angulated fibers will tighten when the vertebrae rotates in either direction, relative to each other. The laminated plies are less firmly attached to each other.

Immersed within the annulus is the nucleus. The healthy nucleus is largely a gel-like substance having high water content, and like air in a tire, serves to keep the annulus tight yet flexible. The nucleus-gel moves slightly within the annulus when force is' exerted on the adjacent vertebrae while bending, lifting, and other motions.

The spinal disc may be displaced or damaged due to trauma, disease, degenerative defects, or wear over an extended period. A disc herniation occurs when the annulus fibers are weakened or torn and the inner tissue of the nucleus becomes permanently bulged, distended, or extruded out of its normal, internal annulus confines. The mass of a herniated or "slipped" nucleus tissue can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases causing the annulus to buckle in areas where the laminated plies are loosely bonded. As these overlapping laminated plies of the annulus begin to buckle and separate, either circumferential or radial annular tears may occur, which may contribute to persistent or disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate back pain from degenerated or herniated discs, the nucleus is removed and the two adjacent vertebrae are surgically fused together. While this treatment alleviates the pain, all discal motion is lost in the fused segment. Ultimately, this procedure places a greater stress on the discs adjacent to the fused segment as they compensate for lack of motion, perhaps leading to premature degeneration of those adjacent discs.

As an alternative to vertebral fusion, various prosthetic discs have been developed. The first prosthetics embodied a wide variety of ideas, such as ball bearings, springs, metal spikes and other perceived aids. These prosthetics are all made to replace the entire intervertebral disc space and are large and rigid. Many of the current designs for prosthetic discs are large and inflexible. In addition, prosthetic disc sizes and other parameters limit the approach a surgeon may take to implant the devices.

For example, many of these devices require an anterior implantation approach as the barriers presented by the lamina and, more importantly, the spinal cord and nerve rootlets during posterior or posterior lateral implantation is difficult to avoid. Anterior implantation involves numerous risks during surgery. Various organs present physical obstacles as the surgeon attempts to access the damaged disc area from the front of the patient. After an incision into the patient's abdomen, the surgeon must navigate around organs and carefully move them aside in order to gain access to the spine. Additionally, the greater vessels are presented during an anterior approach. These greater vessels (the aorta and vena cava) risk exposure and injury during surgery. One risk to the patient from an anterior approach is that their organs may be inadvertently damaged during the procedure. Another risk to the patient from an anterior approach is that their greater vessels may be injured during surgery. These constraints and/or considerations have led to novel prosthetic disc designs as disclosed in U.S. Pat. No. 8,167,948, which is incorporated herein by reference in its entirety.

A posterior approach to intervertebral disc implantation avoids the risks of damaging body organs and vessels. Despite this advantage, a posterior approach raises other difficulties that have discouraged its use. For instance, a posterior approach can introduce a risk of damaging the spinal cord. For example, vertebral body geometry allows only limited access to the intervertebral discs and a posterior approach usually requires the retraction of the spinal cord to one side, or the other, or both during surgery. Because of the spinal chord's importance in the human body, reducing exposure of the spinal cord to injury during surgery is important. Thus, the key to successful posterior or posterior lateral implantation is avoiding contact with the spinal cord, as well as being able to place an implant through a limited area due to the shape of the vertebral bones. These constraints and/or considerations have led to novel prosthetic disc designs as disclosed in U.S. Pat. No. 7,641,666, which is incorporated herein by reference in its entirety.

Another known approach to the intervertebral space is the transforaminal approach. This approach has been used in interbody lumbar fusion surgeries and involves approaching the intervertebral space through the intervertebral foramina. This approach often requires the removal of one facet joint on either the left or right side. After removal, the surgeon gains access to the intervertebral space through the intervertebral foramina. One drawback to this method is that the removal of a facet joint may lead to instability of the spine. Despite this drawback, in many instances the transforaminal approach is favored in that there is reduced risk to the organs and greater vessels (as compared to the anterior approach) and reduced risk to the spinal cord (as to the posterior approach).

All disc replacements, regardless of the approach, require a secure connection between the implant and the implant holder for both implantation and removal purposes. Due to limitations on the available space, disc replacements may only provide one type of connecting mechanism to a holder. Because disc replacement implants move during normal operation, there is a concern, especially during removal, that the discs may be come unaligned or separated and difficult to remove. Due to the large forces involved for removal, a threaded connection may be desirable. For implantation purposes, however, a non-threaded, simple holder may be preferred. Accordingly, there remains a need for an implant connection designed to cooperate with a holder that facilitates both simple implantation and removal of the implant.

After implantation, disc replacements also require some form of primary stability to hold the device in place while bone grows into or onto the endplates and provides a secondary stability over time. The way to achieve primary stability has been the source of some debate. Primary stability may be achieved, for example, by a keel, but keels require extensive bone preparation through the vertebral endplates. The keels need a chisel to cut through the vertebral endplates, which may cause bleeding as well as concerns regarding the fusion of a motion preserving device. Accordingly, there remains a need to provide a design which offers primary stability without causing a significant bony disruption to the vertebral endplates and yet still achieves the required primary and secondary stability.

SUMMARY OF THE INVENTION

To meet this and other needs, intervertebral prosthetic discs are provided with connections for facilitating implantation and removal, and intervertebral prosthetic discs which provide primary and secondary stability over time.

According to one embodiment, an intervertebral prosthetic disc includes a first endplate and a second endplate having both quick connect and threaded connection features. The first endplate has a first surface configured to substantially engage with a first vertebral body and a second surface comprising an articulating surface configured to allow for relative movement of the first endplate. The second endplate has a first surface configured to substantially engage with a second vertebral body and a second surface comprising an articulating surface configured to allow for relative movement of the second endplate. The first surface of the first endplate has a first keel configured to engage with a groove in the first vertebral body. The first keel has a first trailing surface with a first opening extending therethrough. The first opening includes a first bore hole having a first longitudinal axis and a first curved cutout extending obliquely relative to the first longitudinal axis. The first surface of the second endplate has a second keel configured to engage with a groove in the second vertebral body. The second keel has a second trailing surface with a second opening extending therethrough. The second opening includes a second bore hole having a second longitudinal axis and a second curved cutout extending obliquely from the second longitudinal axis. The first and second curved cutouts are configured to receive a first retaining feature and the first and second bore holes are configured to receive a second retaining feature.

The implant feature allows for the implant to be secured with either a quick connection or a threaded connection through one continuous feature. The first retaining feature may include a quick connect holder having a first arm configured to engage the first curved cutout and a second arm configured to engage the second curved cutout. The quick connect holder may provide for a non-threaded, straight-forward, and simple holder, for example, aiding in simple implantation. The first and second bore holes may be threaded such that the second retaining feature is a threaded holder. The threaded holder and connection may provide for a secure connection, for example, assisting in removal of the implant. Thus, the internal features allow for two different types of connections to the implant through a single opening in each of the first and second endplates. These internal features avoid having to use significantly more material volume, external surface area, or needing to use a different space or area for a second tool attachment point. Utilizing two connections in a single opening improves the efficiency of how internal material is used, thereby leading to improved mechanical characteristics of the implant.

One of the first and second keels may have at least one slot extending a length downwardly from a distal edge of the keel to the base of the keel. One of the first and second keels may also include a leading edge that includes a chamfer for aligning and inserting the keel into the groove in the first and second vertebral bodies.

The intervertebral prosthetic disc may include a core element at least partially disposed between the first and second endplates. The core element may have a first contoured surface in communication with and substantially corresponding to the second surface of the first endplate, and a second contoured surface substantially in communication with and substantially corresponding to the second surface of the second endplate. The articulating surface of the second endplate may permit rotation of the second endplate relative to the core element substantially in the sagittal plane. The articulating surface of the second surface of the first endplate may permit rotation of the first endplate relative to the core element substantially in all planes.

The first and second endplates may be constrained to prevent separation of the first and second endplates from each other. The first and second endplates may be constrained to prevent separation of the first and second endplate during linear translation.

According to another embodiment, an intervertebral prosthetic disc includes a first endplate and a second endplate having at least one stability feature. The first endplate has a first surface configured to substantially engage with a first vertebral body and a second surface comprising an articulating surface configured to allow for relative movement of the first endplate. The second endplate has a first surface configured to substantially engage with a second vertebral body and a second surface comprising an articulating surface configured to allow for relative movement of the second endplate. The stability feature may include at least one stabilizing body comprising a first elongated portion having first and second ends, a second elongated portion having first and second ends, the second end of the first elongated portion and the first end of the second elongated portion are integrally formed with each other to form a substantially L-shaped body. The first end of the first elongated portion may be connected to the first or second plate and the second end of the second elongated portion is free to engage the first or second vertebral body.

In a first configuration, the second elongated portion is substantially perpendicular to the first elongated portion to facilitate insertion of the prosthetic disc. A distal end of the second elongated portion may be pointed or sharped to ease insertion into the vertebrae. In a second configuration, the second elongated portion may be compressed closer to the first surface of the first or second endplate to secure the prosthetic disc to the first or second vertebral body. For example, in the second configuration, the second elongated portion may be provided at an angle less than 90° relative to the first elongated portion (e.g., about 45-80°). A portion of the second elongated portion may be serrated, for example, to enhance stability of the stabilizing body in the second, compressed configuration. A transition between the first and second configurations may occur when the stabilizing body is at least partially formed from a shape memory alloy, such as a temperature sensitive shape memory alloy, and the temperature of the stabilizing body reaches body temperature. For example, the shape memory alloy may include a copper-aluminum-nickel alloy or a nickel-titanium alloy (i.e., Nitinol).

The first surfaces of the first and second endplates may be smooth and do not include keels or the like. By eliminating the keels and the need for cutting an opening in the vertebral endplate for a keel and by leaving the vertebral endplate intact, the chances of fracturing the endplate is reduced, and the possibility of additional bleeding on the endplates due to extensive preparation is reduced. Removing the keels also eliminates the need to have high speed mills to prepare the vertebral endplates, which adds to surgical time and complexity.

BRIEF DESCRIPTION OF THE DRAWINGS

The invention will be more readily understood with reference to the embodiments thereof illustrated in the attached figures, in which.

DETAILED DESCRIPTION

Figure 1:
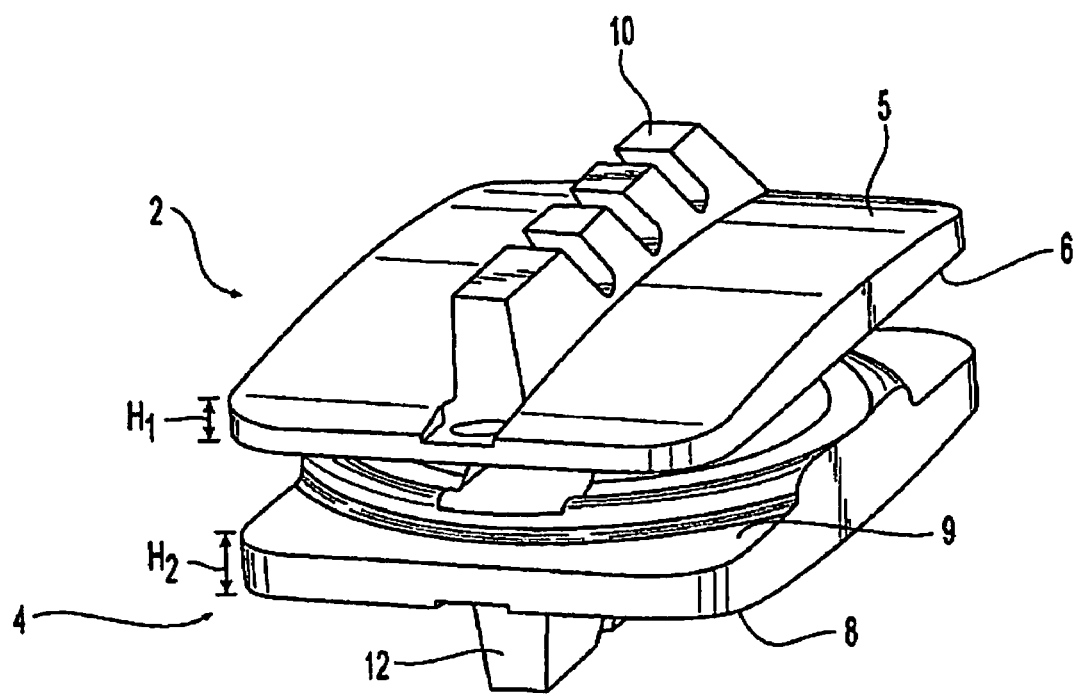
FIG. 1 is an illustration of an embodiment of a prosthetic disc design of the present invention.

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

The present disclosure relates generally to prosthetic spinal discs for replacing a damaged disc between two vertebrae of a spine. In particular, the intervertebral prosthetic discs are provided with two connections for facilitating implantation and removal, and intervertebral prosthetic discs which offer primary and secondary stability, for example, in the form of L-shaped pins or spikes. Various instruments, aids, and other devices for implanting the various prosthetic disc designs are also contemplated.

There are any number of considerations that must be factored into designs for prosthetic discs. In addition to size and configuration parameters that impact the implantation approach, the ultimate goal of any prosthetic disc design is to treat patients with spine problems. In some instances, the prosthetic disc design is used to restore proper vertebral body spacing. In other instances, the prosthetic disc design is used to provide a means by which the vertebral bodies may move relative to each other, either mimicking natural movement or providing increased movement as compared to other treatments such as intervertebral fusion. Finally, any number of other considerations may impact the design of a prosthetic disc including, but not limited to, increasing stability of the spine and decreasing negative biomechanical effects on neighboring vertebrae due to degenerative disease.

The prosthetic spinal discs include the use of fixed and moving instantaneous axis of rotation (IAR) and/or the center of rotation (COR) of one vertebral body with reference to another. The IAR and COR of a healthy vertebral body with respect to another is constantly changing in alt planes because of pushing, pulling, and tethering of the segment through its range of motion by the ligaments, annulus, muscles, facets and other portions of the spine.

Past devices have attempted to mimic or partially mimic natural disc movement by including designs that provide for a moving IAR. These designs, however, typically have been achieved in the past at the expense of a loss of stability of the device. Some examples of prosthetic disc designs having a moving IAR or variable IARs that mimic or partially mimic the natural movement of a health disc are described in U.S. Pat. Nos. 4,759,766; 5,401,269; 6,414,551; 7,621,956; 7,641,666; 8,167,948; and 8,480,746. All references, including publications, patent applications, and patents, cited herein are hereby incorporated by reference to the same extent as if each reference were individually and specifically indicated to be incorporated by reference and were set forth in its entirety herein.

Depending on the approach, the spine may be subjected to increase destabilization as a result of the removal of a facet joint. Additionally, disease or other considerations may lead a surgeon to prefer a prosthetic disc design that does not have a moving IAR. Accordingly, some embodiments of the present invention contemplate prosthetic discs with a fixed IAR. Another advantage of the present disc design relates to the incorporation of stops and other mechanical features of the present invention that reduce the wear and stress on the remaining facet and other structural components of the spine. Generally, past prosthetic disc designs incorporating a ball and socket design with fixed IARs have been known to cause damage to facet joints due to anatomical interferences. The present invention contemplates disc designs that reduce the tendency of fixed IAR prosthetic discs to impact structural wear of the spine.

Other embodiments of the present invention contemplate the use of prosthetic disc designs with a moving IAR, including but not limited to, the three component prosthetic disc designs disclosed in U.S. Pat. Nos. 7,621,956; 7,641,666; 8,167,948; and 8,480,746. In some embodiments, the artificial disc is capable of providing a moving IAR. In one embodiment, the moving IAR achieved is substantially in the sagittal plane. For example, one embodiment of the invention is a prosthetic disc that provides a moving IAR substantially in the sagittal plane so that a patient can more easily flex and extend the spine while limiting the movement of the IAR under lateral bending.

The materials used for different embodiments of the invention will depend to some extent upon the type of surface contact being used as well as the type and extent of wear that may result. Examples of materials that may be used include, but are not limited to, polyethylene (or other elastomeric material) on metal, metal on metal, polyethylene on polyethylene, or ceramic on ceramic. In some embodiments, metal on metal is preferred because there is reduced wear of the prosthetic disc and reduced debris over long-term use. Alternatively, in some embodiments, ceramic on ceramic may be used. In other embodiments, any number of various combinations of materials may be used.

Any prosthetic disc design must consider the type of and range of movements that it will allow. Naturally, the spine is capable of six degrees of freedom: (1) compression, (2) distraction, (3) flexion, (4) extension, (5) lateral bending, (6) rotation, (7) linear translation. Disc designs may be unconstrained, critically constrained, or over-constrained. In an unconstrained device, the range of motion of a prosthetic disc is not limited by any mechanical limits of the prosthetic disc. In an under-constrained device, the prosthetic disc's range of movement is limited to movements outside of the naturally occurring range of movement allowed or permitted by a natural healthy disc. In a critically constrained device, motion is allowed within the physiologic range but limited beyond. An over-constrained device imposes limits on the natural movement. Unconstrained designs of the present invention utilize the various components of the vertebral spine, including muscles, ligaments, facet joints, and other elements of the body to limit the movement of the components of the prosthetic discs. In constrained designs, mechanical stops may be provided to limit the range of movement of the components of the prosthetic disc. The stops may be designed to limit one, two, or more of the various types of movements capable by the prosthetic discs or the natural disc. The present invention contemplates prosthetic disc designs allowing for various degrees of movement, although in some instances, preferred embodiments are constrained in the degree of freedom to limit structural wear of the spine. In alternate preferred embodiments, the design of prosthetic discs of the present invention is constrained to limit the structural wear on a remaining facet.

The articulating surfaces of the prosthetic discs may be comprised of a convex and concave surface. In this embodiment, the prosthetic disc may allow for axial rotation, radial rotation, extension, flexion, and bending of the spine. In some designs, the articulating surfaces may allow for translation of a vertebral segment relative to another. In the prosthetic disc embodiments, the articulating surfaces of the prosthetic disc may be designed to allow for translation in one, two, or more than two directions.

Prosthetic discs may be comprised of two components: a top piece (also referred to as a top endplate) and a bottom piece (also referred to as a bottom endplate) or three components: a top endplate, a core, and a bottom endplate. While for convenience's sake, the designs are described as top and bottom, or superior and inferior, it should be understood that any features associated with one endplate or piece could likewise be associated with the other endplate or piece. Similarly, while the articulating surfaces may be described in one particular manner, i.e. with the top piece made of a convex surface and the bottom piece made of a matching concave surface, one in the art would understand that the type of the articulating surface of any particular endplate, whether the top or bottom, is not important.

Each endplate of the prosthetic disc has an inner and outer surface. The outer surface of an endplate of the prosthetic disc is designed to interact or contact a vertebral body segment. The inner surface of an endplate is designed with an articulating surface. The articulating surfaces may be of a ball and socket design, which allow the inner surfaces of the endplates to articulate with respect to each other. The outer surface of an endplate may be designed to conform to the surface of the vertebral body to which the endplate attaches. Accordingly the outer surface may have a particular shape to coincide with the shape of a vertebral body. Alternatively, the outer surface of an endplate may be curved to conform to the contacting surface of a vertebral body. Alternatively, the outer surface of the endplate may have a keel, nails, spikes, or other structure to contact the vertebral body surface. Alternatively, the outer surface of the endplate may have bores through which fasteners may be placed to anchor the endplate to the contacting vertebral body. In some embodiment the outer surface of an endplate may contain one or more of the features described above.

In addition to providing an endplate surface geometry or configuration that may promote bony in-growth to hold the interfacing surfaces together securely over the long term, these configurations also may help provide short term fixation of the endplate to the vertebral body. For example, a keel may have a wedge shape so that the width of a first end of the keel near the endplate is narrower than the width of the distal end. Once installed, the inverted wedge of the keel helps prevent separation of the endplate from the vertebral body at least until bony in-growth can more securely hold the endplate in place.

To help accelerate and to further promote bony in-growth at the interface between the vertebral body and the endplate, the endplate may be coated with an osteoconductive material and/or have a porous or macrotexture surface. For example, the endplate may be treated with a coating that promotes bone growth. Examples of such coatings include, without limitation, hydroxyl appetite coatings, titanium plasma sprays, sintered beads, or titanium porous coatings.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar parts throughout the several views of the drawings.

As used herein and in the claims, the terms "comprising" and "including" are inclusive or open-ended and do not exclude additional unrecited elements, compositional components, or method steps. Accordingly, the terms "comprising" and "including" encompass the more restrictive terms "consisting essentially of" and "consisting of."

FIG. 1 is an illustration of an embodiment of a prosthetic disc. With reference to FIG. 1, the prosthetic disc has a top endplate 2 and a bottom endplate 4. Top endplate 2 has an outer surface 5 and an inner surface 6. Bottom endplate 4 has an outer surface 8 and an inner surface 9. The prosthetic disc of FIG. 1 may be inserted into the intervertebral space in a patient. When inserted, outer surface 5 of top endplate 2 contacts a first vertebral body (not shown). Similarly, outer surface 8 of bottom endplate 4 contacts a second vertebral body (not shown). As can be seen in FIG. 1, both the top endplate 2 and bottom endplate 4 have raised keels 10 and 12. As can be seen in FIG. 1, the top endplate 2 has a height $H_1$. Likewise, bottom endplate 4 has a height $H_2$. The exact height of the top endplate 2 and bottom endplate 4 may vary from design to design depending on any number of considerations including for example the desired disc height in a patient or the amount of space available for implantation of the device.

In one embodiment, the surgeon is provided a kit with endplates of prosthetic disc designs. The kit may have, for example, one bottom endplate with a set height and various top endplates with different heights. Accordingly, the surgeon may select a top endplate for implantation with the bottom endplate such that the overall height of the prosthetic disc after implantation restores the height of a natural healthy disc. One advantage of providing a kit with more than one top endplate of various heights, is that it allows the surgeon to customize the prosthetic disc with respect to height during surgery. In addition, the surgeon may also test fit various top endplates during surgery. If the disc height does not appear to be desirable, the surgeon may simply substitute the top endplate for another one in the kit, and hence, make adjustments to the prosthetic disc during surgery. Of course, one of skill in the art would understand that kits may be provided where the top endplate has a fixed height and multiple bottom endplates with various heights are provided. Alternatively, the kit may have multiple top and bottom endplates which may have different heights.

Figure 2:
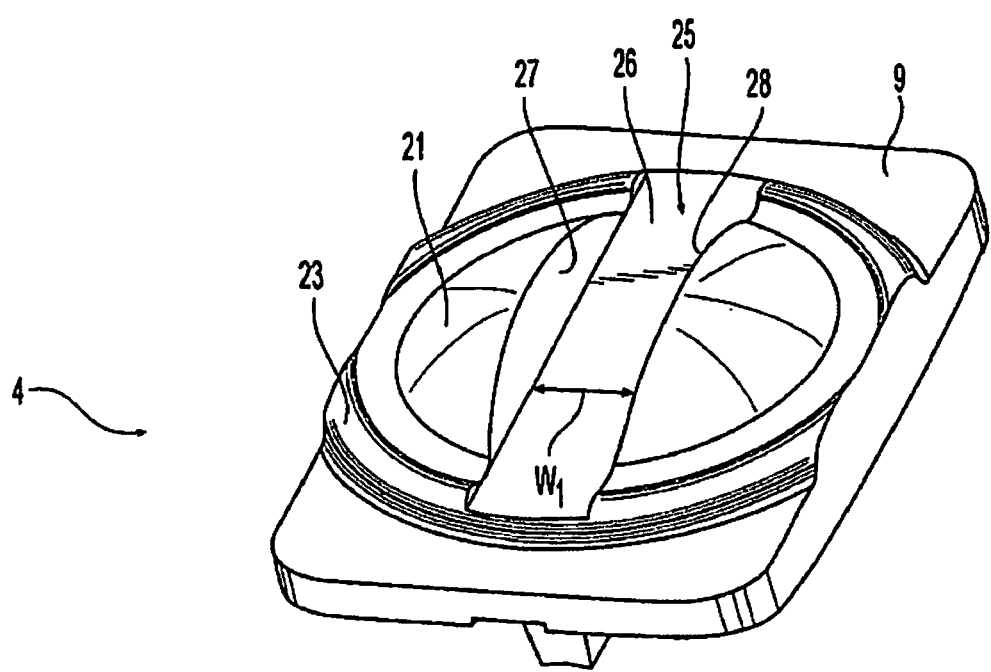
FIG. 2 is an illustration of a bottom endplate of a prosthetic disc design of the present invention.

With reference to FIG. 2, the prosthetic disc designs generally have endplates made with articulating surface. With continuing reference to FIG. 1 and FIG. 2, bottom endplate 4 may have a partially spherical contact surface 21. Partially spherical contact surface 21 may be convex and extend above inner surface 9 of bottom endplate 4. Partially spherical contact surface 21 may be dimensioned to provide a sufficient area over which a top endplate (not shown) may contact. As can be seen in FIG. 2, partially spherical contact surface 21 is partially surrounded by a rim 23, which creates a transition zone between partially spherical contact surface 21 and inner surface 9 of bottom endplate 4.

FIG. 2 further shows one part of a two-part mechanical stop according to one embodiment of the present invention. As seen if FIG. 2, partially spherical contact surface 21 of bottom endplate 4 has a channel 25 extending through the convex partially spherical contact surface 21. Channel 25 has a bottom wall 26 and two side walls 27 and 28. Bottom wall 26 of channel 25 is substantially flat or parallel with interior surface 9 of bottom endplate 4. In alternative embodiments, however, bottom wall 26 of channel 25 may be convex or concave.

Figure 3:
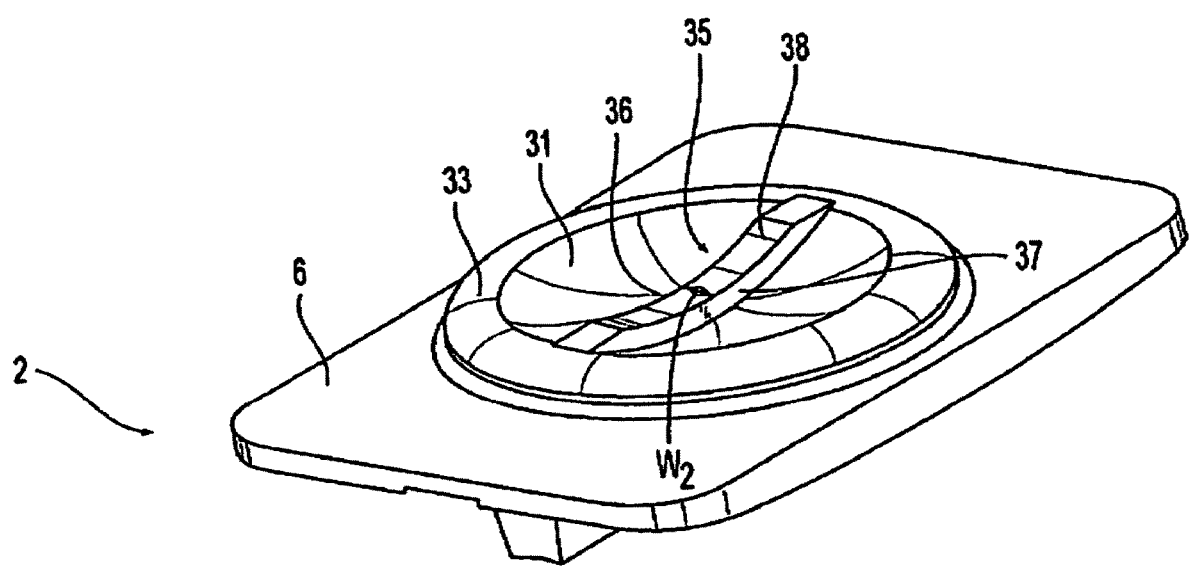
FIG. 3 is an illustration of a top endplate of a prosthetic disc design of the present invention.

FIG. 3 is an illustration of a top endplate of a prosthetic disc according to one embodiment. Top endplate 2 has a partially spherical contact surface 31 that is concave. Partially spherical contact surface 31 may be dimensioned to provide a sufficient area over which a bottom endplate (not shown) may contact. Accordingly and with reference to FIG. 2 and FIG. 3, partially spherical contact surface 31 of top endplate 2 and partially spherical contact surface 21 of bottom endplate 4 are substantially of similar dimension and shape such that when the prosthetic disc is assembled, contact surfaces 21 and 31 mate over an area of each respective surface to create articulating surfaces. The articulating surfaces of this ball and socket type design impart the degrees of movement between top endplate 2 and bottom endplate 4.

As seen in FIG. 3, partially spherical contact surface 31 is at least partially surrounded by rim 33. Rim 33 defines the outer circumference of partially spherical contact surface 31 and creates a transition zone between partially spherical contact surface 31 and inner surface 6 of top endplate 2. As further seen in FIG. 3, partially spherical contact surface 31 contains a raised portion or protrusion 35. Protrusion 35 generally comprises the second part of a two-part mechanical stop. Protrusion 35 runs radially from one point along the outer circumference of partially spherical contact surface 31 to its opposite point through the center of partially spherical contact surface 31. Protrusion 35 extends above partially spherical contact surface 31 and has two side walls 36 and 37 and a bottom wall 38. In FIG. 3, the protrusion is shown with a concave bottom side wall although in alternative designs, bottom wall 38 may be convex or parallel to interior surface 6 of top endplate 2.

FIG. 2 further shows one part of a two-part mechanical stop according to one embodiment. As seen if FIG. 2, partially spherical contact surface 21 of bottom endplate 4 has a channel 25 extending through the convex partially spherical contact surface 21. Channel 25 has a bottom wall 26 and two side walls 27 and 28. Bottom wall 26 of channel 25 is substantially flat or parallel with interior surface 9 of bottom endplate 4. In alternative embodiments, however, bottom wall 26 of channel 25 may be convex or concave.

FIG. 3 is an illustration of a top endplate of a prosthetic disc according to one embodiment. Top endplate 2 has a partially spherical contact surface 31 that is concave. Partially spherical contact surface 31 may be dimensioned to provide a sufficient area over which a bottom endplate (not shown) may contact. Accordingly and with reference to FIG. 2 and FIG. 3, partially spherical contact surface 31 of top endplate 2 and partially spherical contact surface 21 of bottom endplate 4 are substantially of similar dimension and shape such that when the prosthetic disc is assembled, contact surfaces 21 and 31 mate over an area of each respective surface to create articulating surfaces. The articulating surfaces of this ball and socket type design impart the degrees of movement between top endplate 2 and bottom endplate 4.

As seen in FIG. 3, partially spherical contact surface 31 is at least partially surrounded by rim 33. Rim 33 defines the outer circumference of partially spherical contact surface 31 and creates a transition zone between partially spherical contact surface 31 and inner surface 6 of top endplate 2. As further seen in FIG. 3, partially spherical contact surface 31 contains a raised portion or protrusion 35. Protrusion 35 generally comprises the second part of a two-part mechanical stop. Protrusion 35 runs radially from one point along the outer circumference of partially spherical contact surface 31 to its opposite point through the center of partially spherical contact surface 31. Protrusion 35 extends above partially spherical contact surface 31 and has two side walls 36 and 37 and a bottom wall 38. In FIG. 3, the protrusion is shown with a concave bottom side wall although in alternative designs, bottom wall 38 may be convex or parallel to interior surface 6 of top endplate 2.

Whatever the particular design, the mechanical stops are intended to provide constraints on the degrees of movement of the prosthetic disc, i.e., the degrees of movement allowed by the articulating surfaces of the contacting endplates. With continuing reference to FIGS. 2 and 3, channel 25 and protrusion 35 are designed to limit rotation of the prosthetic disc. In this embodiment, channel 25 has a width $W_1$. Protrusion 35 is designed with a width, $W_2$, that is less than $W_1$. The particular widths, i.e., $W_1$ and $W_2$ may vary, although their dimensions will determine the amount of rotation allowed. When assembled, partially spherical contact surfaces 21 and 31 are mated or in contact and protrusion 35 lies or fits within channel 25. Upon rotation, side walls 36 and 37 of protrusion 35 may contact side walls 27 and 28 of channel 25, hence limiting movement. As one of ordinary skill in the art would understand, the respective widths of protrusion 35 and channel 25 will determine the amount of rotation allowed.

Prosthetic disc designs may further contain additional mechanical stops to control or limit movement in other degrees of freedom. For example and with continuing reference to FIGS. 2 and 3, interior surfaces 31 and 21 of top and bottom endplates 2 and 4, respectively, may contain mechanical stops to limit lateral bending, flexion, and extension. As seen in FIGS. 2 and 3, rims 33 and 23 of top and bottom endplates 2 and 4, respectively, may be used to mechanically limit the lateral bending, flexion, and extension. In this embodiment, rims 33 and 23 of top and bottom endplates 2 and 4, respectively, are dimensioned and sized such that during flexion, extension, and/or lateral bending, rim 33 of the top endplate 2 and rim 23 of bottom endplate 4 may contact each other and prevent the articulating surfaces, i.e. partially spherical contact surface 31 of top endplate 2 and partially spherical contact surface 21 of bottom endplate 4, from further articulation.

Figure 4:
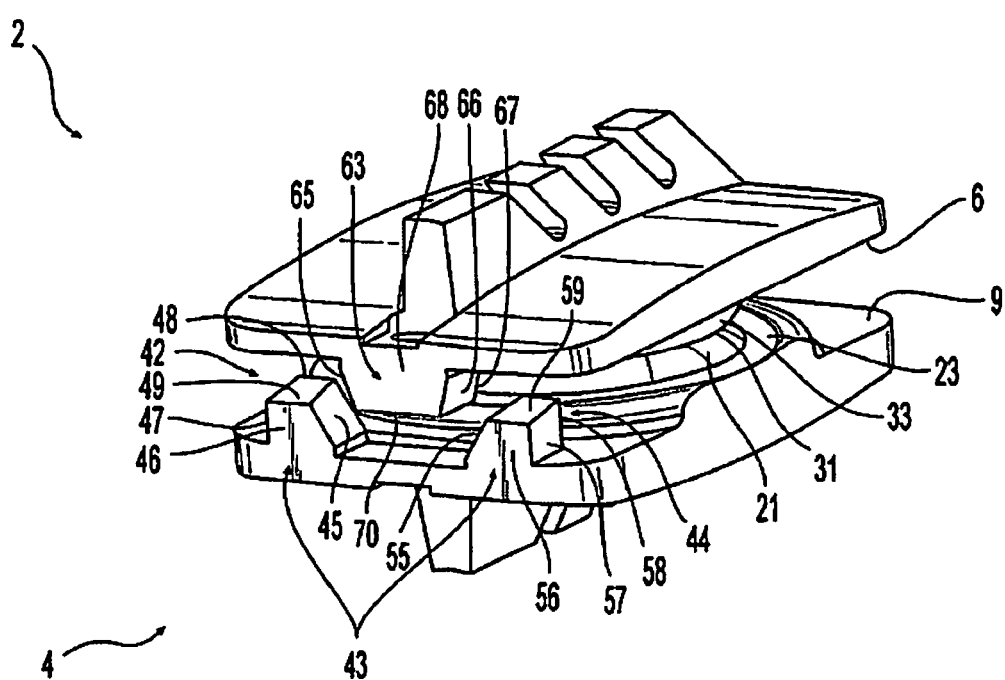
FIG. 4 is an illustration of an embodiment of a prosthetic disc design of the present invention.

In an alternate embodiment, alternative mechanical stops are provided. With reference to FIG. 4, a prosthetic disc design is illustrated with mechanical stops to limit rotation of the respective articulating surfaces. As seen in FIG. 4, partially spherical contact surface 21 of bottom endplate 4 and partially spherical contact surface 31 of top endplate 2 are in contact and do not contain any additional channels or protrusions as in previous designs. Instead, mechanical stops are formed on the interior surfaces 6 and 9 of the top endplate 2 and bottom endplate 4.

As seen in FIG. 4, interior surface 9 of bottom endplate 4 contains a first part 43 of a two-part rotational stop. In this particular embodiment, the rotational stop is located on the posterior portion of the prosthetic disc. A first part 43 of the rotational stop is located on the interior surface 9 of lower endplate 4. First part 43 of the rotational stop is made of a first and second protrusion 42 and 44, respectively, that extends from the interior surface 9 of bottom endplate 4. Protrusion 44 has five walls, four side walls 45, 46, 47, 48 and one top wall 49. Similarly, protrusion 42 has five walls, four side walls 55, 56, 57, 58 and a top wall 59. In this particular embodiment of the prosthetic disc design, side walls 45 and 55 have angled surfaces as seen in FIG. 4. The second part of the rotational stop is located on the interior surface 6 of top endplate 2. This part of the rotational stop is a protrusion that extends below the interior surface 6 of top endplate 2. Top endplate protrusion 63 has five walls, including four side walls 65, 67, 68, 69 and one bottom wall 70. In this particular embodiment of the prosthetic disc design, side walls 65 and 66 have angled surfaces as seen in FIG. 4.

With continuing reference to FIG. 4, the first and second protrusions 42 and 44 of bottom endplate 4 and protrusion 63 of top endplate 2 are not in contact when the prosthetic disc is assembled and in its neutral position (shown in FIG. 4). During rotational movement, however, protrusion 63 of top endplate 2 will contact one of the first or second protrusions 42 or 44 of bottom endplate 4. For example, in one direction of rotation, side wall 65 of protrusion 63 of top endplate 2 will contact side wall 45 of first protrusion 42 of bottom endplate 4, thus, limiting the movement or the articulating surfaces of the top and bottom endplates 2 and 4. As seen in FIG. 4, angled side walls 45, 55 and 65, 67 may cause the endplates to move as in flexion. Accordingly, this design provides a softer or more cushioned rotational stop than would be encountered if the side walls were perpendicular to their respective interior surfaces. In alternative embodiments, the angles formed between the side walls and interior surfaces may be acute, in which case the rotational stops might additionally serve to create the opposite movement described above, namely, extension. As one of skill in the art would understand, the placement of the rotational stops and angles of the side walls may be varied to achieve various results and degrees of movement.

Preferably, the height of first and second protrusions 42 and 44 of bottom endplate 4 are sized, in conjunction with the height of protrusion 63 of top endplate 2, such that the upper walls 49 and 59 of first and second protrusions 42 and 44 of bottom endplate 4 do not interfere or contact interior surface 6 of upper endplate 2 during flexion, extension, or lateral bending. Rather, rims 23 and 33 of upper endplate 2 and lower endplate 4 act to limit movement in those directions. Similarly, protrusion 63 of top endplate 2 is sized such that bottom wall 69 does not come into contact with interior surface 9 of bottom endplate 4. The height of the rotational stop protrusions 42, 44, 63 may be larger or smaller depending on the amount of flexion, extension, and lateral bending allowed by the rims on the interior surfaces of the top and bottom endplate as discussed above. Alternatively, in embodiments where rims are not provided as mechanical stops for flexion, extension, and lateral bending, the heights of the protrusions may be sized such that top walls 49 and 59 and bottom wall 69 do come into contact with the interior surfaces of the top and bottom endplate, thus also serving as mechanical stops for flexion, extension, and lateral bending. Of course, one of skill in the art would understand that to limit all three types of movement (in addition to the rotational limitation) in a prosthetic disc design without rims, the design may require an additional set of protrusions located at an anterior portion of the prosthetic disc.

Figure 5:
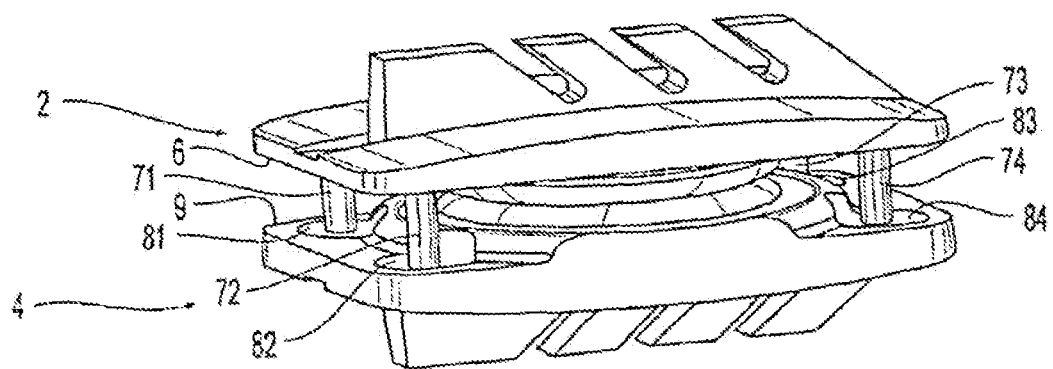
FIG. 5 is an illustration of an embodiment of a prosthetic disc design of the present invention.

FIG. 5 is an illustration of another embodiment of a prosthetic disc design with an alternative mechanical stop design. As seen in FIG. 5, rotational stops may be provided located on the interior surface 6 of upper endplate 2. In this embodiment, four cylindrical shaped pins 71, 72, 73, 74 are located on the four corners of interior surface 6 of top endplate 2. Bottom endplate is formed with holes 81, 82, 83, 84 on interior surface 9 of bottom endplate 4 directly below cylindrical shaped pins 71, 72, 73, 74, respectively. In the prosthetic disc's neutral position, cylindrical pins 71-74 extend at least partly within the cavities created by holes 81-84, respectively. Accordingly, during rotational movement the exterior surfaces of pins 71-74 contact the interior surfaces of holes 81-84 limiting movement. In some designs, holes 81-84 extend entirely through bottom endplate 4. In alternative designs, holes 81-84 may be blind holes, i.e. where holes 81-84 do not extend through bottom endplate 4.

As would be understood by one of skill in the art, holes 81-84 are sized in conjunction with pins 71-74, to provide for the freedom of movement desired. Similarly, where holes 81-84 are blind holes, in some designs the depth of holes 81-84 and the length of pins 71-74 may be dimensioned such that pins 71-74 contact the bottom portion of their respective holes 81-84 during flexion, extension, and/or lateral bending. This additional stop mechanism may work in conjunction with the rim design previously described or may substitute the rims and be the primary mechanical stop to limit or constrain flexion, extension, and/or lateral bending. In alternative embodiments, only one pin and one hole may be provided. In alternative embodiments, more than one hole and pin is provided. Furthermore, it would be understood by one of skill in the art that the pins and holes need not be cylindrical in shape but may also take various shapes yet still serve as rotational stops. Similarly, one of skill in the art would understand that of the various mechanical stops described, any number of variations and combinations may be employed to limit movement of the articulating surfaces of the prosthetic disc designs.

In an embodiment of the present invention the prosthetic disc design is rotationally constrained and the endplates are allowed to rotate 1° in either direction from its neutral position. In alternative embodiments the prosthetic disc design is rotationally constrained and the endplates are allowed to rotate 10° or more in either direction from its neutral position. In some embodiments of the present invention, the prosthetic disc design may be unconstrained in one, two, or more than two degrees of freedom. In some embodiments of the present invention, the prosthetic disc design may be constrained in one, two, or more than two degrees of freedom.

In one embodiment, the upper and lower portions of a disc assembly may be configured with a keel that can engage with or contact a neighboring vertebral body. One advantage of providing a keel is that it may be used to guide the assembly into position during insertion into a treated area of the spine. For example, a channel or groove may be cut out of a vertebral body to facilitate insertion of a keel. Then, a physician may insert the assembly into the vertebral body so that the keel slides in the groove or channel. The keel and grove may be substantially linear or straight, or alternatively, may be curved or arched so that the assembly rotates and slides into position. The ridges or keels and corresponding channels or grooves also may be straight or curved to match the desired insertion path of the assembly. The grooves or channels formed in a vertebral body may help achieve the proper orientation and distance of the assemblies and provide for a secure anchoring of the endplate or endplates.

The cross-sectional profile of the keel may have different shapes. For instance, the cross-sectional profile of the keel may have the shape of a wedge, a truncated wedge, a rectangle, or a square. The channel or groove may be cut to have a cross-sectional profile corresponding approximately to the shape of the keel. One advantage of the keel having a truncated wedge cross-section is that a similarly shaped channel or groove may ensure that the keel engages with the bony surface. This configuration may also provide increased resistance to expulsion of the disc assembly.

Figure 6:
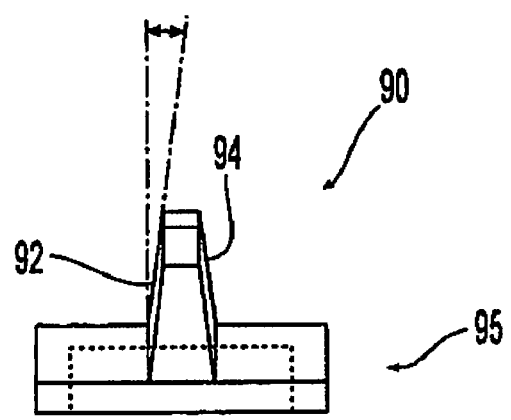
FIG. 6 is an illustration of a keel of a prosthetic disc design of the present invention.

In one embodiment, the cross-section of a ridge or keel may be triangular or have a truncated triangular shape. For example, as shown, in FIG. 6, keel 90 is of a truncated triangular shape. The height of keel 90 may vary, but may be configured with sloped sides 92 and 94, as shown in FIG. 6, of about 5° from the longitudinal plane. The height of keel 90 may vary, but in general is designed to provide sufficient contact area once inserted in the vertebral body to anchor endplate 95. The keel may be sized such that any groove or channel cut into the vertebral body to accommodate the keel does not substantially impact the structural integrity of the vertebral body.

The use of one or more keels may also increase bone to implant surface contact, thereby decreasing the likelihood that the assembly will shift or move about of position. In one embodiment, the increase in surface contact may be about 5% or more, which in another embodiment the increase may be about 15% or more.

Over time, it is believed that the stability of the disc assembly in the treated area will further increase as bone growth engages with outer surfaces of the disc assembly. To facilitate this growth and increased stability, all or part of the surfaces of the disc assembly that engages or otherwise contacts bone may be treated to promote bony in-growth. For instance, titanium plasma may be provided on the keel or other portions of the assembly to provide a matrix for bone growth. In addition, the keel may be configured with notches, slots, or openings formed along its length. As bone grows into these openings, the disc assembly will become more securely anchored in place.

Figure 7:
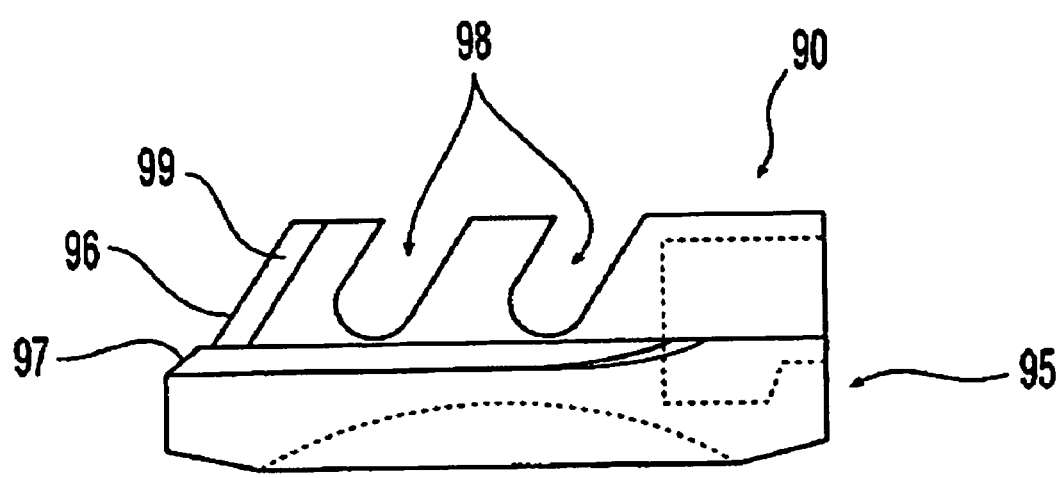
FIG. 7 is an illustration of a keel of a prosthetic disc design of the present invention.

As a disc assembly is first inserted into a treated area, it may need to be repositioned, rotated or otherwise moved. For instance, repositioning the disc assembly may be needed so that the keel can properly engage with the channel or groove. As shown in FIG. 7, keel 90 of endplate 95 has an angled first leading edge 96. Additionally, endplate 95 may be configured with a second leading edge 97 that does not contain part of keel 90. Thus, in one embodiment the assembly can be partially inserted into the treated area without keel 90 engaging with or contacting the vertebral body. In one embodiment, the length of second leading edge 97 is from about 1 mm to about 10 mm, while in another embodiment second leading edge 97 is from about 2 mm to about 5 mm. Alternatively, the length of second leading edge 97 may be from about 1% to about 20% of the length of the endplate 95 on which it is disposed, or may be from about 2% to about 10%. The length of the endplate 95 may be determined by measuring the longitudinal central axis of the portion or endplate on which second leading edge 97 is disposed.

In addition, referring again to FIG. 7, keel 90 may have first leading edge 96 that is sloped or gradually increases in height. As seen in FIG. 7, first leading edge 96 is sloped. Providing a ramped first leading edge 96 may aid in aligning and inserting keel 90 into a groove or channel formed in a vertebral body.

As mentioned previously, the keel of a disc assembly may be configured to promote or permit bony in-growth that may help hold the disc assembly in place more securely. FIG. 7 further illustrates an embodiment of keel 90 having a plurality of slots or cuts 98 formed in it. In FIG. 7, slots 98 may extend at an angle, such as from about 5° to about 40° off from a vertical direction, and more preferably from about 10° to about 30°. Keel 90 may have two or more, or even three or more slots or cuts. One skilled in the art would appreciate that other configurations may also be used to promote bony in-growth that might help further secure the disc assembly in place. For instance, the keel may have holes or apertures drilled into it, longitudinal or horizontal slots may be formed, and the sidewalls of the keel may be textured with one or more grooves or channels that do not extend fully through the keel to the opposing sidewall.

In addition, the face of the keel that is first inserted into a groove or channel may have a taper or chamfer. One potential advantage of configuring a keel with a taper or chamfer on its face is that it may assist in aligning the keel with the opening of the channel or groove. In addition, a chamfered or tapered face may help reduce drag forces and undesired cutting or gouging of the channel or groove as the keel is pushed toward its final position. As seen in FIG. 7, the face of keel 90 is configured with a chamfer 99 to aid in the insertion of the prosthetic disc.

Figure 8:
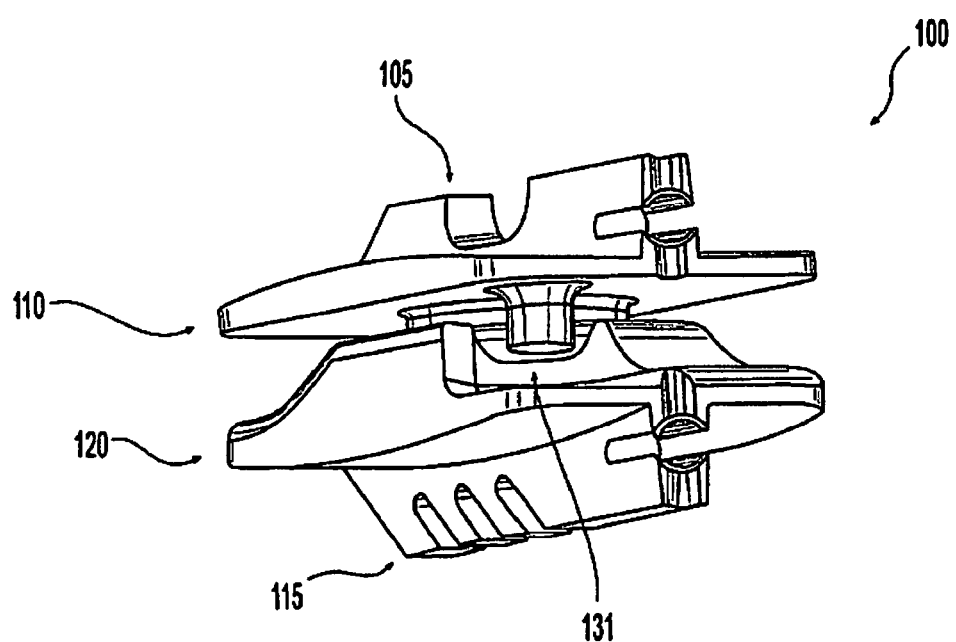
FIG. 8 is a perspective view of another embodiment of the present invention.

In an alternate embodiment, different prosthetic disc designs may be provided. With reference to FIG. 8, an alternate embodiment of the present invention is provided. As seen in FIG. 8, a prosthetic disc 100 is provided having an upper endplate 110 and lower endplate 120. Upper endplate 110 may be configured with a keel 105, as discussed previously, to guide the endplate during implantation and increase contact area between the upper endplate 110 and the upper vertebral body (not shown). Similarly, lower endplate may be configured with a keel 115, to guide the endplate during implantation and increase the contact area between lower endplate 120 and the lower vertebral body (not shown).

Figures 9, 10:
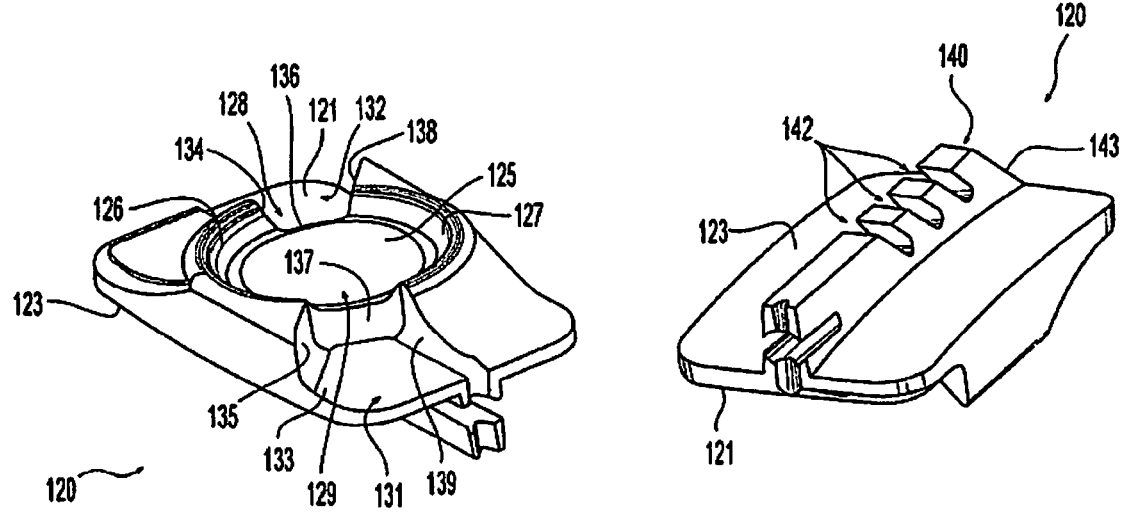
FIG. 9 is a perspective view of an endplate of the embodiment of FIG. 8.
FIG. 10 is a perspective view of an endplate of the embodiment of FIG. 8.

With continuing reference to FIG. 8, FIGS. 9 and 10 illustrate the lower endplate. In FIG. 9, the lower endplate 120 is illustrated showing its superior surface 121, whereas in FIG. 10, the lower endplate is illustrated showing its inferior surface 123, i.e. the surface which contacts the lower vertebral body. As seen in FIG. 9, the lower endplate is configured with a partially spherical surface 125, which is concave and provides a seating surface configured to contact with the convex, partially spherical surface of the upper endplate (described below). Disposed about concave partially spherical surface 125 of lower endplate 120 is a partially conical rim that forms sidewalls 126 and 127 to the concave partially spherical surface 125. Disposed about the perimeter rim of the concave, partially spherical surface 125, are two opposing windows 128 and 129 formed out of, or interrupting, sidewalls 126 and 127.

As seen in FIG. 9, window 129 leads to a cavity 131 that is has an inferior surface 133 and three sidewall surfaces 135, 137, and 139. While partially hidden in FIG. 9, one of skill in the art would understand that window 128 leads to cavity 132, which is similarly formed with sidewall surfaces 134, 136, and 138. Cavities 131 and 132 are recesses formed within lower endplate 120 that are configured to interact with stops on the upper endplate, as described in more detail below.

With reference to FIG. 10, lower endplate 120 is shown having an inferior surface 123 upon which keel 140 is formed. The keel extends generally the length of the lower endplate 123 and is disposed generally along the midline of lower endplate 120. Keel 120 may have notches 142 formed within the keel body to provide areas into which bone may grow, and hence, provide a mechanism for increasing the attachment of lower endplate 123 to the vertebral body. Similarly, keel 140 may be formed with a leading edge 143 that is slanted towards the center of lower endplate 120. This leading edge helps during insertion by providing a favorable contact surface as the prosthetic disc is inserted into the vertebral space.

Figures 11, 12:
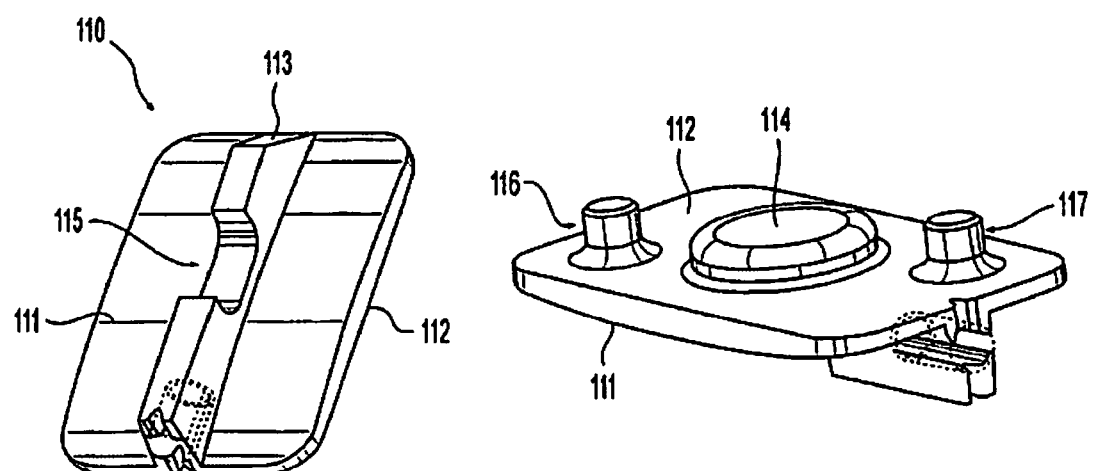
FIG. 11 is a perspective view of an endplate of the embodiment of FIG. 8.
FIG. 12 is a perspective view of an endplate of the embodiment of FIG. 8.

With reference to FIGS. 11 and 12, upper endplate 110 is shown. In FIG. 11, the upper endplate 110 is shown with a view of its superior surface 111, whereas in FIG. 12, upper endplate 110 is shown with a view of its inferior surface 112. As can be seen in FIG. 11, the upper endplate has a keel 113, similarly positioned and configured as keel 140 of lower endplate 120. One difference in this embodiment, however, is that keel 113 of upper endplate 110 may have a window or cut-out 115 formed within keel 113. The cut-out 115 of keel 113 is a cavity disposed generally in the center portion of keel 113. Cut-out 115 is preferably symmetrical and extends along keel 113 in equal directions from the center of the prosthetic disc. As a positioning feature, the cut-out is most effective if the center of cut-out 115 is the same as the center of upper endplate 110 and prosthetic disc 100. In these instances, as one of skill in the art would understand, when the profile of prosthetic disc 100 is viewed in the medial-lateral plane, the center of cutout 115 corresponds to the center of the prosthetic disc. The positioning feature allows a surgeon to position the prosthetic disc within the intervertebral space, regardless of the angle at which the prosthetic disc was placed. Because the window remains visible in a profile view along a variety of angles, the center of the cut-out can be used to position the prosthetic disc within the vertebral space. In this way, the cut-out provides a way to position the prosthetic disc within the intervertebral space in a consistent and simple manner, which is independent of the angle of insertion. This feature may also be used after implantation of the prosthetic disc during follow up visits to track the position of the prosthetic disc postoperatively.

With reference to FIG. 12, the inferior surface 112 of upper endplate 110 is shown. As seen in FIG. 12, a partially spherical convex surface 114 extends in the inferior direction from the inferior surface 112 of upper endplate 110. Partially spherical convex surface 114 of upper endplate 110 is configured to engage with partially spherical concave surface 125 of lower endplate 120 when the prosthetic disc is assembled. In this manner, the contacting surfaces, i.e. partially spherical concave surface 125 and partially spherical convex surface 114, may articulate with respect to each other. The articulating surfaces provide the relative rotation of the adjacent vertebral bodies, above and below the prosthetic disc. The partially spherical nature of the contacting surfaces provides the fixed IAR and COR previously described above.

As can be further seen in FIG. 12, the inferior surface 112 of upper endplate 110 is configured with two stops 116,117 that extend downward from the inferior surface 112 of upper endplate 110. In this embodiment, the stops are shaped as truncated cylinders, although in alternate embodiments the stops may take the form of any variety of shapes and configurations. As seen in FIG. 12, the stops are spaced apart from the partially spherical convex surface 114 of upper endplate 110. As further seen in FIG. 8, when upper endplate 110 and lower endplate 120 are assembled, stops 116 and 117 of upper endplate 110 fit within cavities 128 and 129 of lower endplate 120. While FIG. 8 is shown with the prosthetic disc in its neutral position, one of skill in the art would understand, that upon axial rotation of the endplates with respect to each other, the stops would interact with the sidewalls of cavities 131,132 and limit rotation of the endplates relative to each other. As seen in FIG. 9, sidewall 135 provides a surface against which stop 117 abuts. As further seen in FIG. 9, sidewall 139 is not necessarily configured to provide a contact surface for stop 117. This is so because in this particular design, the remaining facet acts as a limiting mechanism for rotation in that direction. Accordingly, one of skill in the art would understand that depending on the facet removed, this embodiment may be designed in alternative configurations such that a mechanical stop is integrated into the prosthetic disc design to compensate for the removed facet, while relying on the remaining facet to act as a natural stop for rotation in the opposite direction.

As one of skill in the art would understand, the sizes of the cavities and stops may be varied to allow for the range of movement desired. Accordingly, in some instances it may be desirable to limit axial rotation to between about 1° to about 10°. In alternative embodiments axial rotation is limited to between about 3° to about 7°, or between about 4° to about 6°, or to between about less than 1° to more than 5°.

Figure 13:
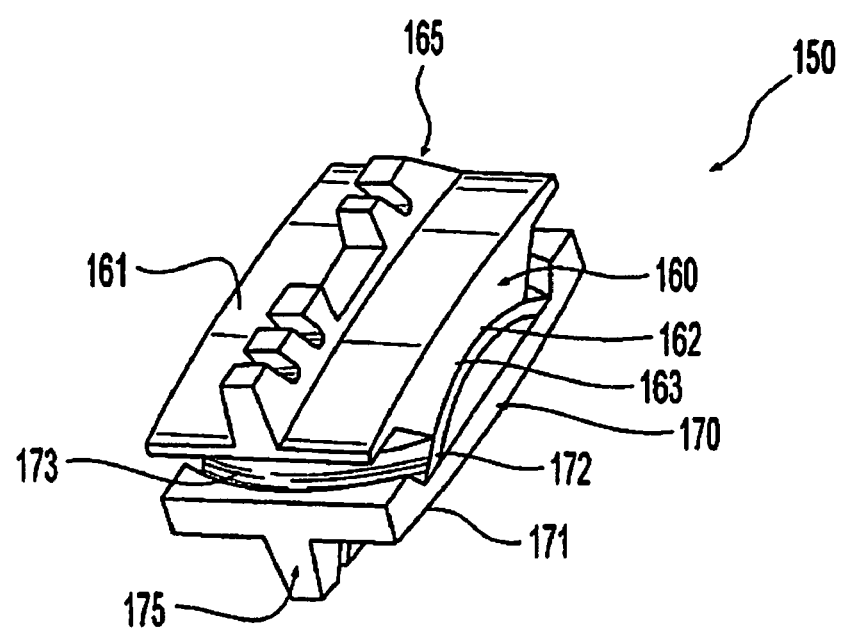
FIG. 13 is a perspective view of an embodiment of the present invention.

In an alternate embodiment, prosthetic disc 150 has an upper endplate 160 and lower endplate 170. With reference to FIG. 13, upper endplate is configured having a superior surface 161 and inferior surface 162. Superior surface 161 of upper endplate 160 is configured with a keel 165, which may contain similar features as previously described. Inferior surface 162 of upper endplate 160 has a partially spherical concave surface 163. With continuing reference to FIG. 13, lower endplate is configured with an inferior surface 171. Inferior surface 171 of lower endplate 170 is configured with a keel 175, which also may contain similar features as previously described. Superior surface 172 of lower endplate 170 has a partially spherical concave surface 173.

Figure 14:
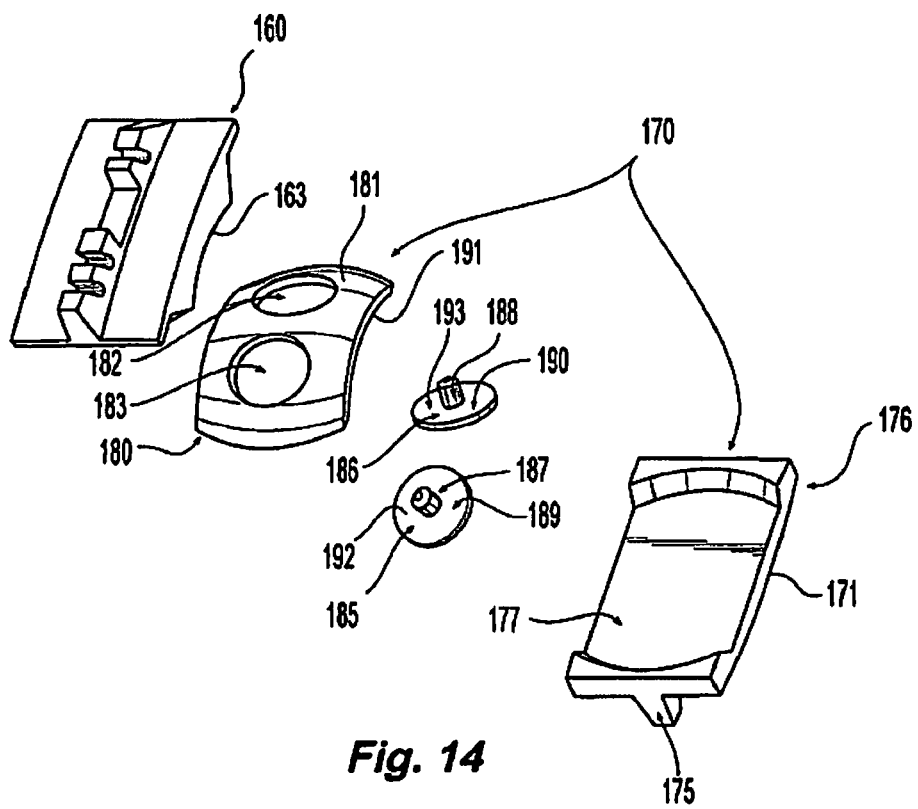
FIG. 14 is an exploded view of the embodiment of FIG. 13.

With continuing reference to FIG. 13, FIG. 14 illustrates an exploded view of the embodiment of FIG. 13. As seen in FIG. 14, lower endplate 170 is constructed from two pieces to from the lower endplate 170. First portion 176 comprises the inferior surface 171 having a keel 175 and superior surface 177 configured to receive a second portion 180. Second portion 180 is a partially spherical wedge having a discreet thickness and curvature. The curvature of partially spherical convex wedge 180 corresponds to the partially spherical concave surface 163 of the inferior surface 162 of upper endplate 160, thus forming a partially spherical convex surface 181. While any number of methods may be used, one non-limiting method of attaching first portion 176 to second portion 180 may be welding. In this example, the lower endplate 170 is formed of a first portion 176 and second portion 180, wherein after attachment of the second portion 180 to the first portion 176 a cavity is formed between the first portion 176 and second portion 180 of lower endplate 170. As seen in FIG. 14, second portion 180 further has two bore holes 182, 183 disposed on its partially spherical convex surface 181.

Stops 185,186 may be used to limit the articulating between the partially spherical concave surface 163 of upper endplate 160 and the partially spherical convex surface 181 of second portion 180 of lower endplate 170. Stops 182,183 have two portions, an attaching portion 186,187 and a washer portion 188,189, respectively. These portions may be integrally formed as one piece or may be formed as separate pieces. In an embodiment, attaching portion 186 is shaped as a cylindrical rod as seen in FIG. 14. Attaching portion 186 is configured to attach to upper endplate 160 on one end and attach to washer portion 188 on the other end. The attachment may be by any number of different means including welding, fixation compounds, threaded attachments or others. When assembled, attaching portion 186 is fixedly attached to the partially spherical concave surface 163 of upper endplate 160. Additionally, washer portion 188 is fixedly attached to attaching portion 186 after upper endplate 160 and lower endplate 170 have been assembled, i.e., partially spherical concave surface 181 and partially spherical convex surface 163 are in contact. In this embodiment, attaching member 186 is attached to the upper endplate 160 such that when the prosthetic disc is assembled, attaching members 186,187 pass through bore holes 182,183 respectively. Washer members 188, 189 are configured to contact or abut the lower surface 190 of partially spherical wedge 180.

Washer members 188, 189 are also configured such that the upper surfaces 191, 192 of washer members 188, 189 are sized such that washer members 188, 189 will not pass through bore holes 182, 183. Accordingly as one of ordinary skill in the art would understand, when assembled, partially spherical convex surface 181 and partially spherical concave surface 163 may articulate with respect to each other but will be limited by the interaction between the solid perimeters of bore holes 182,183 and their interaction with attaching portions 186, 187 of stops 186, 185 respectively. Similarly, washer portions 188, 189 act to limit separation of the upper endplate 160 and lower endplate 170.

As should be apparent from the foregoing description the size of the attaching members 186, 187 and/or the bore holes 182,183 may be adjusted to increase or decrease the amount of articulating that may be experienced between the partially spherical surfaces 163,181. Additionally, one of ordinary skill in the art would understand that the configuration of bore holes 182,183 and/or attaching members 186,187 may differ, which would impact the degrees of freedom of the articulating surfaces 163,181. For example, where the bore holes are dimensioned to be generally of elliptical shape, the articulating surfaces may rotate in greater amounts along the long access of the elliptical bore hole as compared to the short axis. The present invention contemplates the use of differently sized bore holes and/or attaching members to create prosthetic discs with customized degrees of rotation along any number of parameters, whether it be increased flexion/extension, increased lateral bending, etc.

Figure 15:
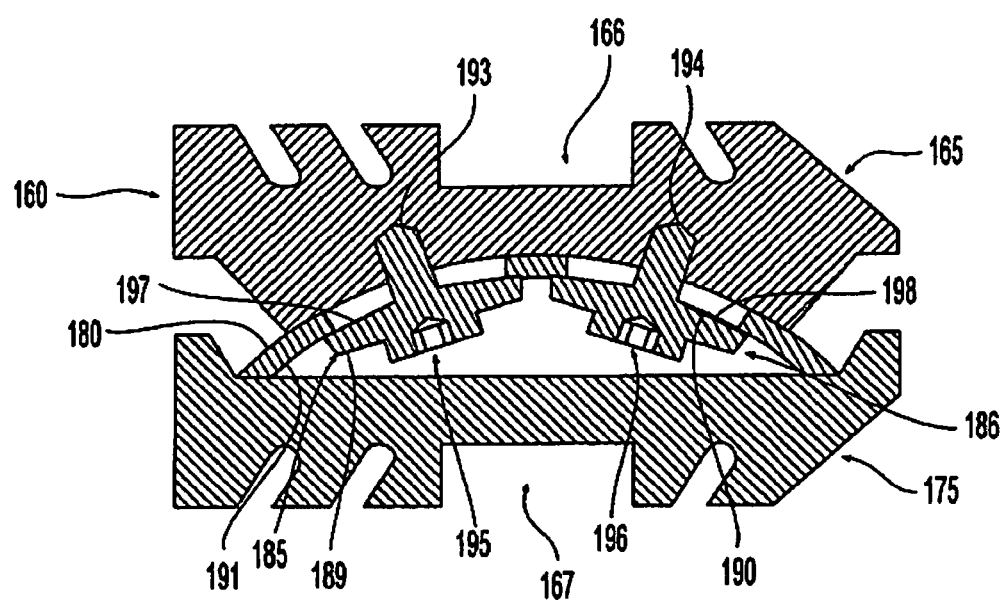
FIG. 15 is a cross sectional view of the embodiment of FIG. 13.

With reference to FIG. 15, a cross sectional view of an assembled prosthetic disc of the embodiment of FIGS. 13 and 14 is shown. As seen in FIG. 15, stops 185, 186 may be formed with a threaded end on stops 185, 186. Similarly, upper endplate 160 may be formed with threaded cavities 193,194 into which stops 185,186 may be inserted. Stops 185, 186 may be configured with engagement areas 195, 196 to drive stops 185, 186 into threaded cavities 193, 194 of upper endplate 160. In this particular embodiment, engagement areas 195, 196 take the form of hexagonal heads for a hexagonal driver (not shown). As also seen in FIG. 15, upper surfaces 197,198 of washers 188,189 of stops 185, 186 may correspond to the curvature of lower surface 190 of wedge 181 of lower endplate 170. In FIG. 15, one may also see how keels 165, 175 are formed with windows 166, 167 to aid positioning of the prosthetic disc as described previously.

Figure 16:
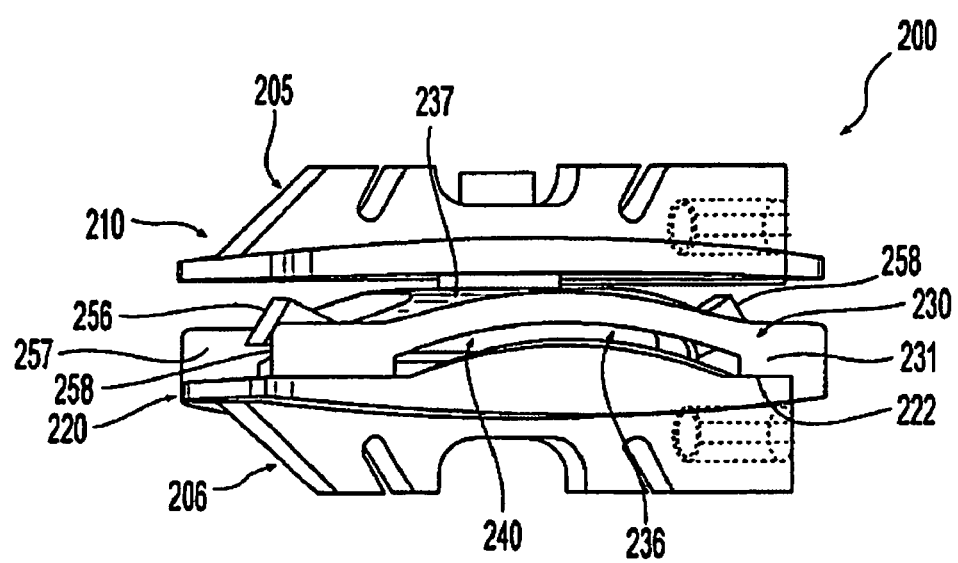
FIG. 16 is a perspective view of an embodiment of the present invention.

With reference to FIG. 16, an alternate embodiment of a prosthetic disc is shown. Prosthetic disc 200 may be configured with upper endplate 210 having a keel 205 with features similar to those described previously. Bottom endplate 220 may similarly be configured with a keel 206 having features as described above.

Figure 17:
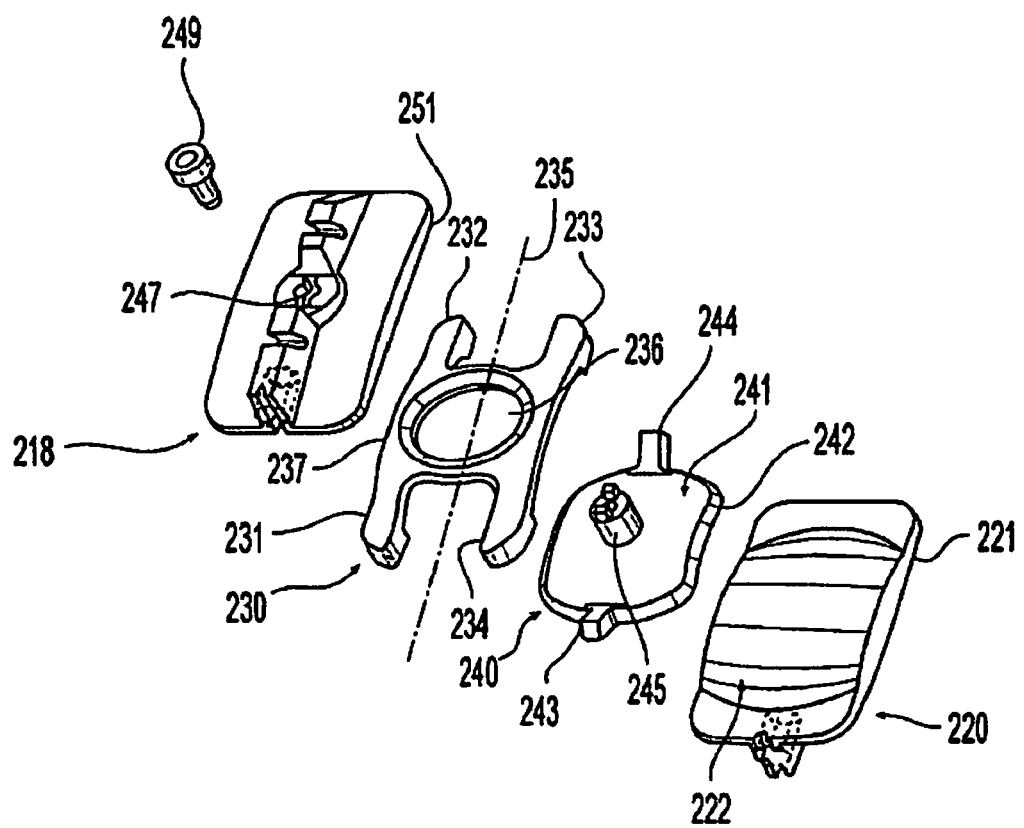
FIG. 17 is an exploded view of the embodiment of FIG. 16.

Referring to FIG. 17, bottom endplate 220 may have a lower surface 221 and upper surface 222. As seen in FIG. 17, upper surface 222 of bottom endplate 220 may be a partially spherical convex surface. Interposed between top endplate 210 and bottom endplate 220 are two intermediate portions 230,240. First intermediate portion 230 may have a generally circular portion from which four arms 231, 232, 233, 234 may extend tangentially along the latitudinal axis 235 of the prosthetic disc. First intermediate portion 230 may be formed with a bore hole 236 disposed centrally as shown in FIG. 16. Arms 231-234 are designed to attached to lower endplate 220 as described in more detail below.

Figure 18:
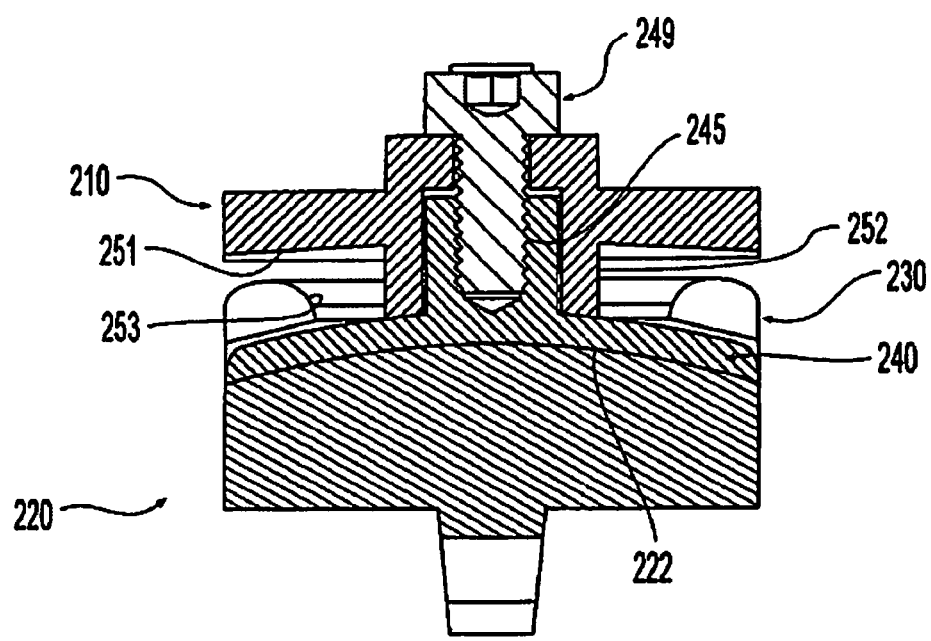
FIG. 18 is a cross sectional view of the embodiment of FIG. 16.

Second intermediate portion 240 may be generally circular in shape and may have an upper surface 241 and lower surface 242. Lower surface 242 of second intermediate member 240 is a partially spherical convex surface and may be configured to engage upper surface 222 of lower endplate 220. Lower surface 242 of second intermediate member 240 and upper surface 222 of lower endplate 200 may articulate with respect to each other in a ball and joint fashion to allow movement of adjacent vertebra relative to each other. Second intermediate portion 240 may also have protruding members 243, 244 extending from the proximal and distal ends of second intermediate portion 240, which are designed to interact with first intermediate member 230 as described in more detail below. As seen in FIG. 17, second intermediate member 240 may have a linking member 245 positioned centrally on the upper surface 241 of second intermediate member 240. In this particular design, post 245 is configured with a unique interlocking design at the superior end of post 245. Respectively, upper endplate 210 may be configured with a receiving area 247 designed to cooperate with the interlocking design of post 245. Accordingly, when assembled, second intermediate portion 240 is capable of being fixedly attached to upper endplate 210. In the embodiment illustrated in FIG. 17, the unique interlocking design of post 245 and the receiving area 247 of upper endplate 210 not only provide for a fixed connection, but also prevent the second intermediate member 240 from rotating with respect to upper endplate 210. Accordingly, to the extent the upper endplate 210 is capable of moving when attached to a vertebral body (not shown), second intermediate member 240 will move with upper endplate 210. Also as seen in FIG. 17, a fastener 249 may be provided to secure the connection between upper endplate 210 and second intermediate member 240. In this case, the fastener is an exteriorly threaded fastener that can partially pass through the receiving area 247 of upper endplate 210 and engage an internally threaded blind hole within post 245 of second intermediate portion 240. As seen in FIG. 18, lower surface 251 of upper endplate 210 may be configured with a collar 252 that is configured to receive post 245 of second intermediate portion 240. Collar 252 adds stability to the connection between the second intermediate portion 240 and the upper endplate 210.

Returning to FIG. 16, first intermediate portion 230 is fixedly attached to bottom endplate 220. As can be seen in FIG. 16, arm 231 is attached to the upper surface 222 of bottom endplate 220. First intermediate portion 230 may be generally curved to correspond to the curvature of articulating surfaces of the prosthetic disc, i.e. upper surface 222 of lower endplate 220 and lower surface 242 of second intermediate portion 240. First intermediate portion 230 may also be formed such that a cavity 236 is created between parts of the aims and generally circular portion 237 as seen in FIG. 16. As one of ordinary skill in the art would understand, a similar cavity 238 may be formed on the opposing side. Accordingly, cavities 236,238 provide space within which portions of the second intermediate portion 240 may fit.

Referring to FIG. 18, a cross section view of the prosthetic disc of FIG. 16 is shown. In this view, fastener 249 is inserted and connects upper endplate 210 and second intermediate member 240. First intermediate member 230 is connected (connection not shown in cross section) to lower endplate 210. When assembled, second intermediate member 240 is captured by the first intermediate member 230. Even though second intermediate member 240 is captured, first intermediate member 230 is formed such that first intermediate member 230 may still articulate relative to the partially spherical convex surface 222 of lower endplate 220. As can be seen by FIG. 18, however, the degree of articulation between the respective endplates may be limited by at least the interaction of post 245 and sidewall 253 of bore hole 236 of first intermediate member 230. Accordingly, as one of ordinary skill in the art would understand, bore hole 236 and post 245 may be configured in various sizes and dimensions to control the amount of articulating between first intermediate portion 230 and lower endplate 220. First intermediate member 230 also prevents the separation of the upper endplate 210 and lower endplate 220 as the first intermediate member 230 captures the second intermediate member 240, which is fixedly attached to upper endplate 210.

Returning to FIG. 16, protruding members 256,258 are shown extending from second intermediate member 240. Protruding members 256,258 may extend from second intermediate member 240 at an angle, in the superior direction. As seen in FIG. 16, protruding member 256 is configured such that upon axial rotation of the prosthetic disc, protruding member 256 may contact sidewalls 257,258 of arms 232,233 of first intermediate member 230. Accordingly, protruding members 256,258 may acts as stops or limits on the degree of axial rotation of the prosthetic disc. As one of ordinary skill in the art would understand, protruding members 256,258 and arms 231-234 may be sized and dimensioned to vary the degree of axial rotation permitted by the prosthetic disc.

Figure 19:
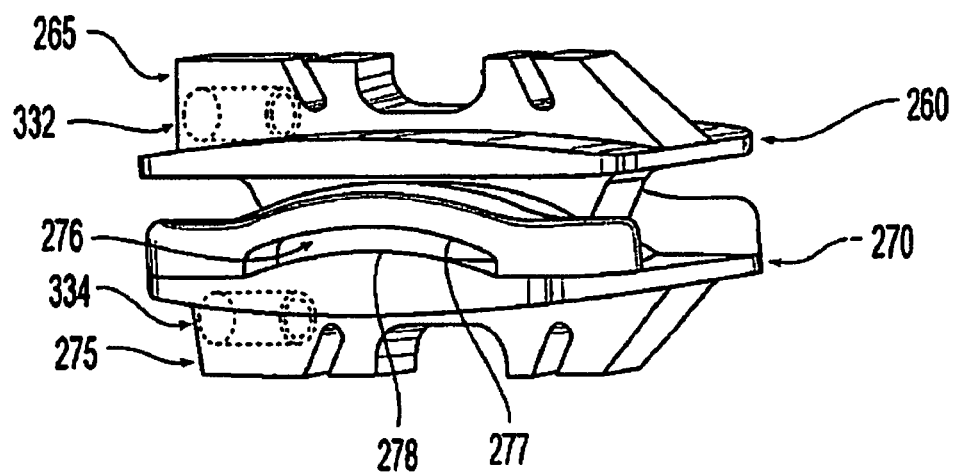
FIG. 19 is a perspective view of an embodiment of the present invention.
Figure 20:
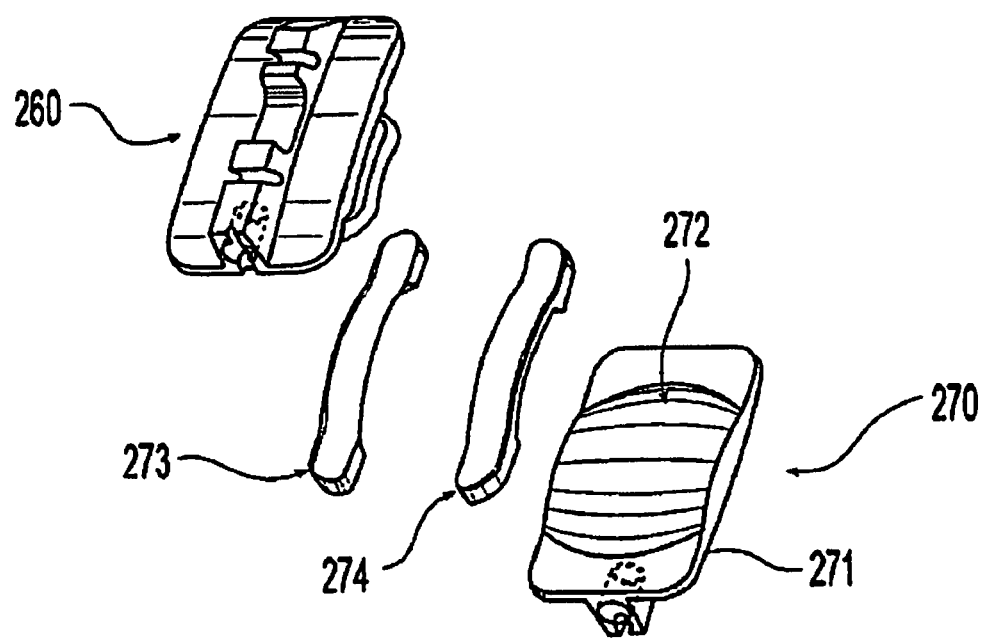
FIG. 20 is an exploded view of the embodiment of FIG. 19.

Referring to FIG. 19, an alternate embodiment of a prosthetic disc is shown having a top endplate 260 and bottom endplate 270. Top endplate 260 may have a keel 265 with features similar to those described above. Bottom endplate 270 may also have a keel 275 with features similar to those described above. With reference to FIG. 20, an exploded view of the present prosthetic disc embodiment is provided. As seen in FIG. 20, the prosthetic disc has a top endplate 260 and bottom endplate 270. Bottom endplate 270 has a lower surface 271 and upper surface 272. Upper surface 272 of bottom endplate 270 is a partially spherical convex surface. Attached to the upper surface 272 of bottom endplate 270 are two side rails 273,274 that run the length of lower endplate 270 and are disposed at either side of the prosthetic disc as shown in FIGS. 19 and 20. Side rails 273,274 are each attached at two different points on the upper surface 272 of lower endplate 270. Side rails 273,274 may be curved to match the curvature of partially spherical convex surface 272. As seen in FIG. 19, between attachment points at the ends of rail 273, a window 276 is created. Window 276 has an upper border 277 that is defined by curved rail 273 and a lower border 278 that is defined by the partially spherical convex surface 272 of lower endplate 270. One of ordinary skill in the art would understand that a similar window would be formed on the other side of the prosthetic disc.

Figure 21:
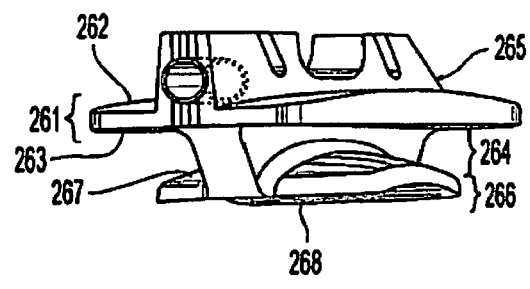
FIG. 21 is perspective view of an endplate of the embodiment of FIG. 20.

Referring to FIG. 21, top endplate 260 is shown. Top endplate 260 has three portions connected to each other. Top portion 261 has an upper surface 262 and lower surface 263, with keel 265 attached to the upper surface 262. Extending from the lower surface 263 of top portion 261 of upper endplate 260 is a middle portion 264 that extends generally along an axis of the top portion 261 and extends in the inferior direction. Middle portion 264 is configured to support bottom portion 266 of top endplate 260. As seen in FIG. 21, bottom portion 266 is connected to middle portion 264, with the middle portion creating a link between top portion 261 and bottom portion 266. Bottom portion 266 has an upper surface 267 and lower surface 268. Lower surface 268 of bottom portion 266 of upper endplate 260 is a partially spherical concave surface. Partially spherical concave surface 268 generally corresponds to partially spherical convex surface 272 of lower endplate 270. As one of ordinary skill in the art would understand, upon assembly of the prosthetic disc of the present invention, partially spherical concave surface 268 and partially spherical convex surface 272 may articulate with respect to each other, allowing the upper endplate 260 and lower endplate 270 to articulate as well. When inserted into the intervertebral space, the present design allows the vertebral bodies to move or rotate in all planes with respect to each other.

Figure 22:
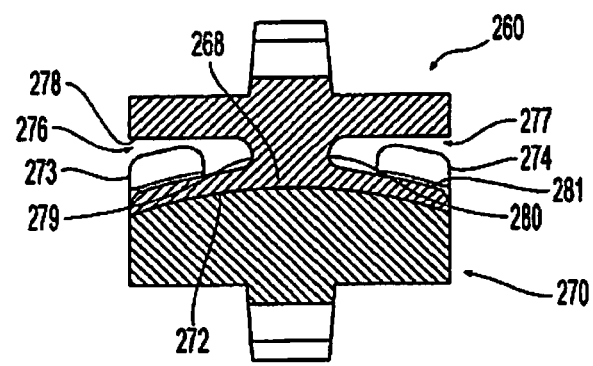
FIG. 22 is a cross sectional view of the embodiment of FIG. 20.

With reference to FIG. 22, a cross section of the embodiment of FIG. 19 is shown. In FIG. 22, the interaction between partially spherical concave surface 268 and partially spherical convex surface 272 is seen. Furthermore, FIG. 22 shows rails 273, 274 disposed between areas 276,277, which are defined by the bottom surface 278 of top portion 261, side surfaces 279,280 of middle portion 264, and upper surface 281 of bottom portion 266 of the top endplate 260. As one of ordinary skill in the art would understand, rails 273, 274 serve to prevent the top endplate 260 and bottom endplate 270 from separating. This feature provides a constrained design that adds stability and rigidity to the overall prosthetic disc. Not only is the device constrained from tension, i.e. separation along the longitudinal axis of the spine, but the constrained design prevents sheer translation separation, i.e. separation of the components of the prosthetic disc as a result of linear translation. Furthermore, the interaction between bottom portion 266 and rails 273,274 as well as the interaction between rails 273,274 and middle portion 264 serve to limit the range of rotation allowed by the articulating surfaces 268,272. Accordingly, the prosthetic disc may be designed to provide a range of rotation. As one or ordinary skill in the art would understand, any number of changes may be made to the size, dimension, or shape of the rails, bottom portion, and/or middle portion to control the range of motion permitted by the prosthetic disc. In one embodiment, the prosthetic disc is capable of axial rotation of between about 1° and 3°. In alternative embodiments, the prosthetic disc is capable of axial rotation of between about 1° and 5°. Alternatively, the prosthetic disc is capable of axial rotation of between 1° and 15°.

One consideration applicable to some embodiments, include the desire to maintain the same degree of rotations irrespective of disc position. This may be the case when the prosthetic disc is placed into the intervertebral space through a transforaminal approach. As the prosthetic disc is seated within the vertebral space at an angle offset from either the anterior-posterior axis of the vertebral bodies and/or the medial-lateral axis of the vertebral bodies, it may be desirable to provided uniform degrees of freedom between the articulating surfaces of the prosthetic disc to accommodate natural movement in the anterior-posterior direction and medial-lateral direction as well as provided for uniform degrees of freedom for coupled motion. This freedom of movement must be designed in conjunction with the shape of the prosthetic disc such that the shape of the disc, its stops, and other structural features do not limit the degrees of freedom in one particular direction more than in others.

Another consideration in some of the embodiments contemplates the design of prosthetic discs in shapes that complement the implantation approach. For example, prosthetic discs of a rectangular shape are particularly well configured for insertion at an oblique angle. Because the transforaminal window is small, rectangular shaped prosthetic discs provide a slim profile allowing easier insertion of the disc into the intervertebral space. Furthermore, these unique shapes also provide sufficient disc surface area to form stable contacts with the bone of the intervertebral space. Additionally, certain sizes provide improved stability of the disc itself by providing sufficient area for the articulating surface such that their respective movement is stable. All of these factors lead to disc designs with shape characteristics that make them particularly well suited for a transforaminal implantation, i.e. implantation at an oblique angle to the anterior-posterior or medial-lateral approaches. It has been found that prosthetic discs with a Length to Width ratio of about 2 to 1 are particularly well suited for transforaminal implantation in that said discs fit within the transforaminal window and provide optimum contact areas for bone contact and articulating surface area contacts. Thus for example, in one embodiment, the prosthetic disc has a length of 30 mm and a width of 15 mm. In alternative embodiments, the prosthetic disc has lengths between about 20 and 40 mm and widths of between about 8 and 20 mm.

With respect to each embodiment herein described, it would be apparent to one of ordinary skill in the art that the particular directions and configurations of the various surfaces can be modified and interchanged. Accordingly, the upper endplate may be the lower endplate and vice versa. Similarly, stops may be formed on either or both endplates. Additionally, keels may be on both or none of the endplates. Moreover, the prosthetic discs of the current invention may additionally contain any number of other features including for example, titanium sprays or other coatings or surface deposits that promote or help bony ingrowth/ongrowth. Similarly, the endplates themselves may be formed, in whole or in part, of materials or contain materials that promote bony ingrowth/ongrowth. Also, the various embodiments disclosed herein are not limited to construction out of any particular materials although metal on metal designs are one variety contemplated.

As disclosed herein are methods for inserting a prosthetic disc assembly into the intervertebral space. In general, the method may involve removal of a fact, preparation of the intervertebral space, creation of one or more pathways, and insertion of a prosthetic disc via the transforaminal approach. Specialized tools for performing said methods are also disclosed.

Prior to insertion of the prosthetic disc, a surgeon must create as window into the disc space. When approaching the intervertebral space from an oblique angle, a facet and number and other components of the body, such as muscles and ligaments, must be accounted for. Accordingly, in an embodiment of the present invention a unilateral facetectomy is performed.

Figure 23:
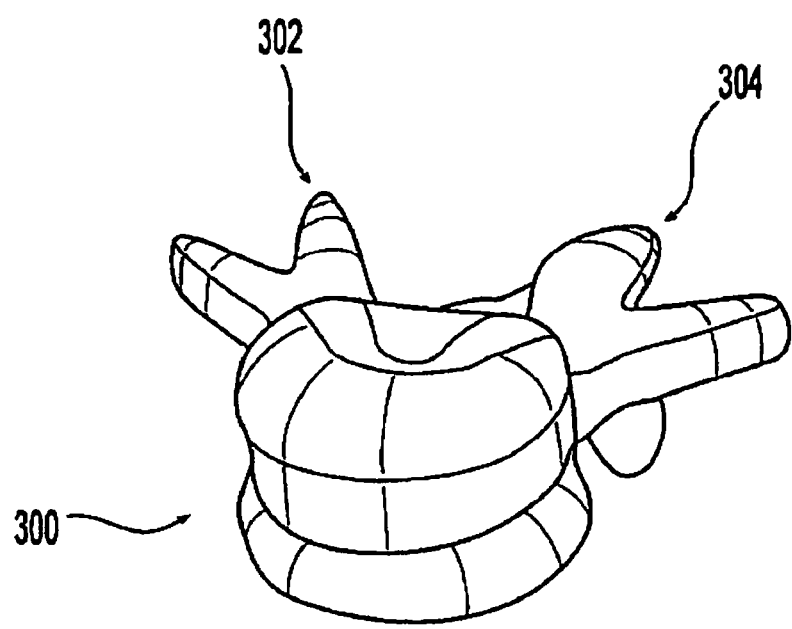
FIGS. 23-24 are perspective views of a representative vertebral body.
Figure 24:
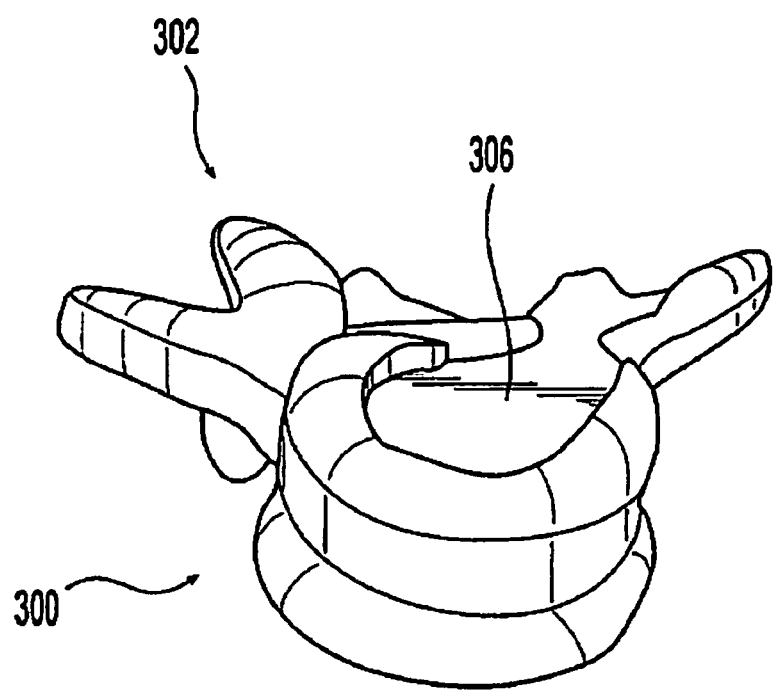

With reference to FIG. 23, a vertebral body 300 is shown. Vertebral body 300 may be from any part of the spine, although the methods herein are particularly suited to lumbar areas of the spine. As seen in FIG. 23, only lower vertebral body 300 is shown. FIG. 23 also shows facets 302 and 304. With reference to FIG. 24, facet 304 has been removed by a surgeon. As seen in FIG. 24, the entire facet has been removed to gain access to the intervertebral space. As further seen in FIG. 24, a surgeon may further prepare the bony surface of the vertebral body by scraping or cutting the surfaces of the bone. As one of skill in the art would understand, a total facetectomy is not necessarily required. Depending on the size and configuration of the prosthetic disc being inserted, a surgeon may perform a partial facetectomy. The amount of the facet removed may be varied from one patient to the next, as the surgeon simply needs a large enough window to insert the prosthetic disc assembly.

In general, prior to insertion of the prosthetic disc, the intervertebral space may be further prepared to receive the prosthetic disc assembly. In one embodiment, a surgeon may perform a total discectomy, in which substantially the entire disc between the two vertebrae is removed. Alternatively, a surgeon may perform a partial discectomy, in which only a portion of the disc is removed. Partial discectomies typically leave a portion of the annulus of the disc intact on the anterior portion of the intervertebral disc space. The present invention is not limited to any particular type of discectomy, whether complete, partial or otherwise.

In an embodiment, another prepatory step in the process of inserting a prosthetic disc according to the present invention may include preparation of the upper and lower surfaces of the vertebral bodies. In this step, a surgeon may scrape the upper and lower surfaces of the vertebral bodies. As seen in FIG. 24, lower surface 306 is shown having been prepared to receive the prosthetic disc. Scraping the surfaces may cause some bleeding, which may improve the chances of bony growth into/onto the inserted assemblies.

In another embodiment, the disc space is prepared by inserting various tools to help loosen the muscles and ligaments that keep the disc space together, referred collectively to as separator tools.

Figure 25:
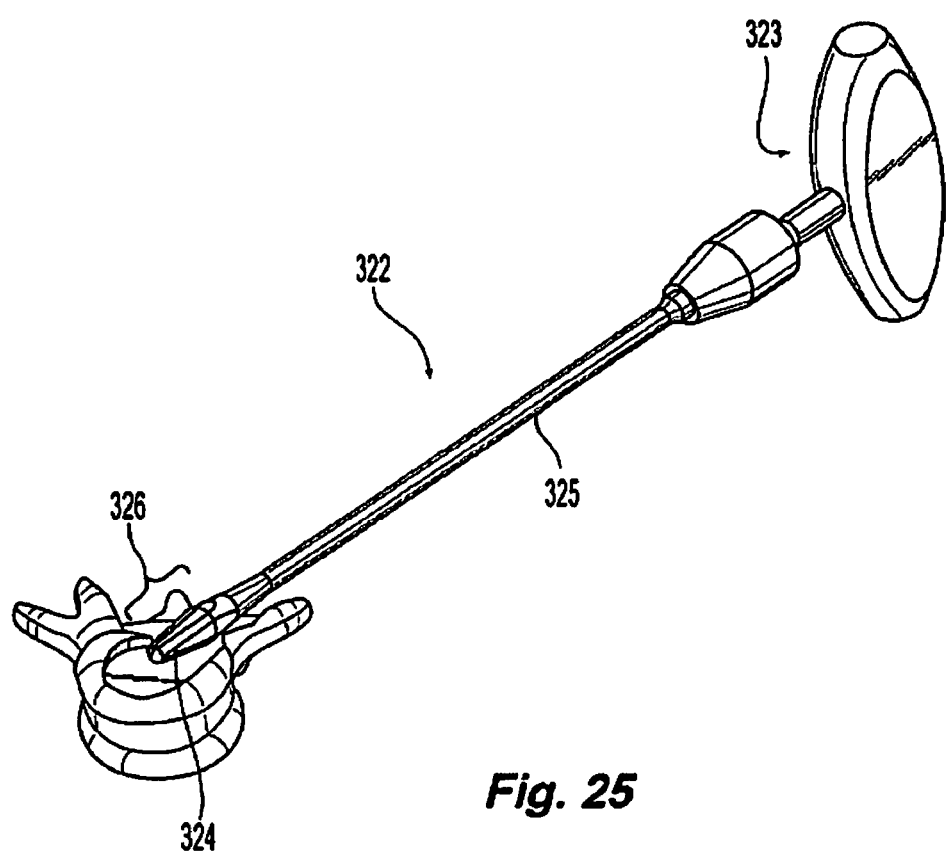
FIG. 25 is a perspective view of a separator according an embodiment of the present invention.

In an embodiment, a dilator may be provided. With reference to FIG. 25, a dilator is shown. As seen in FIG. 25, dilator 322 is similar to paddle distractor 308 except that the end of dilator 322 is configured as a generally regular pyramid. Dilator 322 also has a handle 323 and elongated shaft 325. As one of skill in the art would understand, the shape and configuration of the dilator can aid the surgeon in preparing the disc space by serving as a wedge as the dilator is inserted into the intervertebral space. As further seen in FIG. 25, demarcations 324 along the generally pyramid area 326 correspond to the thickness or width of the area at that point. Thus, a dilator with widths or thickness between 5 mm and 20 mm may be used and the surgeon may distract the intervertebral space by a desired amount by inserting the dilator to the appropriate depth. In an embodiment of the present invention, a set of dilators may be provided that correspond to a range of distraction sizes. For example, in one embodiment, a surgeon may be provided with three dilators that contain a range of sizes of about 6-12 mm, 8-14 mm, and 10-16 mm.

As one of skill in the art would understand, handle 323 may be releasably attachable such that a surgeon may use the same handle for different dilators. As one of skill in the art would understand, a kit may be provided that contains both dilators and paddle distractors. In this embodiment, a single handle may be used for both the different dilators and different paddle distractors. Furthermore, a surgeon may use one type of separator during surgery or the other. Similarly, a surgeon may use both during the procedure.

Figure 26:
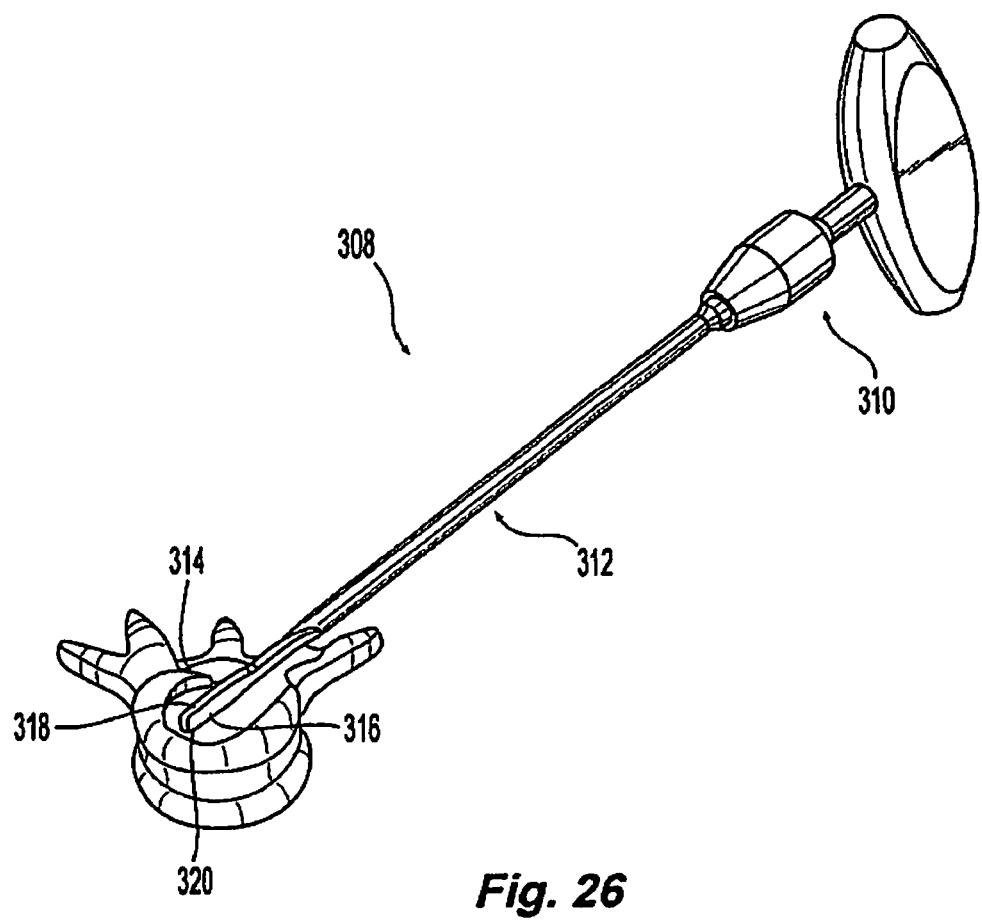
FIG. 26 is a perspective view of a separator according to an embodiment of the present invention.

In an alternate embodiment of the present invention, a paddle distractor may be used. With reference to FIG. 26, a paddle distractor 308 is provided. Paddle distractor 308 may have a handle 310 that is attached to an elongated shaft portion 312. As one of skill in the art would understand, handle 310 may be detached from shaft 312. At the end of elongated shaft portion 312, paddle distractor 308 has an area shaped as a paddle 314, or an area that is wider than it is thick. The length of paddle area 314 may vary, although one of skill in the art would recognize that said length would be sized appropriately so as to enter the intervertebral space without interfering with surrounding tissue or other internal body parts. The shape of the paddle area allows a surgeon to insert the instrument in one direction, i.e. generally flat or so that face 316 of paddle area 314 is generally parallel to the upper and lower surfaces of the upper and lower surfaces of the vertebral bodies between which it is being inserted. Once inserted, a surgeon may rotate handle 310 in turn causing paddle area 314 to rotate within the vertebral space. As sides 318 and 320 contact the upper and lower surfaces of the vertebral bodies, the disc space is distracted and the muscles and ligaments are loosened. This helps prepare the disc space for insertion of the trial.

As one of skill in the art would understand, the size and shape of the paddle distractor may vary and various sized instruments may be provided to accommodate different areas of the spine or distraction preferences by the surgeon. Furthermore, distractors of various sizes may be used to within the same space to distract the space in a stepwise fashion. As the handle is releasably attached, a single handle may be provided with a set of paddle areas such that a surgeon may select different sizes according to surgeon preferences. While any number of sizes may be used, in one embodiment a set of paddle areas with widths of 7 mm to 20 mm, with a separate paddle for each millimeter, is provided. In some embodiments, a paddle area for each possible trial is provided.

After preparing the intervertebral space the next step performed according to one embodiment, a surgeon determines the appropriate size of the assembly to use in the procedure as well as the desired position of the assembly. The present invention contemplates tools and assemblies of various sizes to help a surgeon determine the appropriate prosthetic disc to implant. Trials, of various sizes, are commonly used in this type of surgery to "test fit" items inserted into intervertebral spaces. For example, trials may have lengths between about 20 mm and 40 mm; heights between about 5 mm and 20 mm; and widths between about 8 mm and 20 mm. In one embodiment of the present invention, trial size approximately matches prosthetic disc size. In other embodiments, a kit may be provided with trials, tools, and discs of various sizes.

Figure 27:
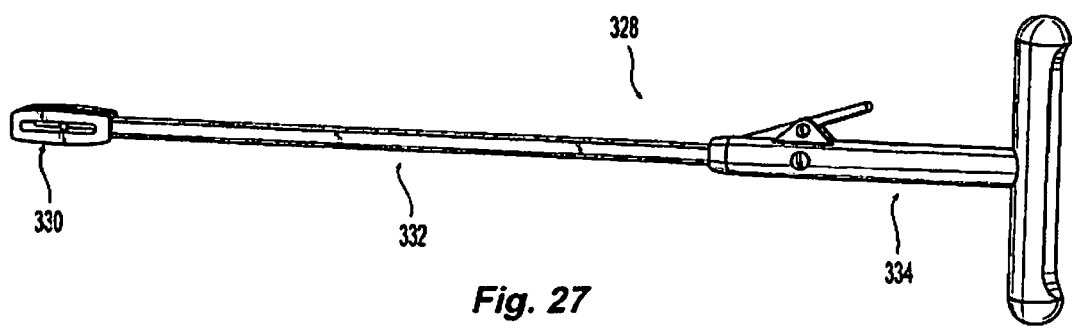
FIGS. 27 and 27A is a perspective view of a trial according to an embodiment of the present invention.
Figure 27A:
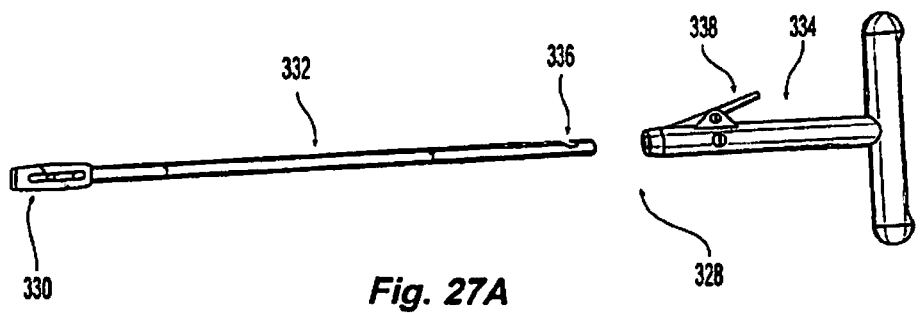

With reference to FIG. 27, a trial 328 is shown. Trial 328 has a head portion 330, elongated shaft portion 332, and handle portion 334. With reference to FIG. 27A, handle portion 334 is releasably attached to elongated shaft portion 332. As seen in FIG. 27A, elongated shaft portion has an engagement area 336, which engages with lever 338 of handle portion 334. As one of skill in the art would understand, any number of different mechanisms may be used to releasably attach handle portion 334 to elongated shaft portion 332.

Figure 28:
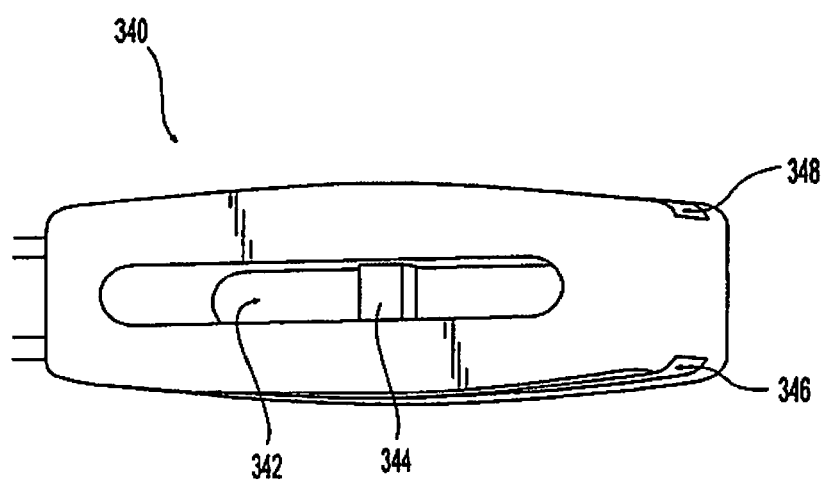
FIG. 28 is a perspective view of a trial head according to an embodiment of the present invention.

With reference to FIG. 28, head portion 340 is shaped to approximate the height and size of the prosthetic disc to be inserted. Head portion 340 of trial 328 is also configured to allow a surgeon to precisely position the head portion with in the vertebral space. As the final position of the prosthetic disc assembly is dependent on or based on the positioning of the trial, a surgeon may desire to be able to position the trial within the vertebral space at a specific location. Accordingly in an embodiment of the present invention and as seen in FIG. 28, head portion 340 has an elongated bore hole 342 running through head portion 340. This creates window 342 in head portion 340. As further seen in FIG. 28, a center post 344 is placed at the center of head portion 340. Accordingly as one of skill in the art would understand, this configuration allows a surgeon to use imaging tools during surgery to position head portion 340 of trial 328 in a desired position. For example, during surgery a surgeon may take radiological images of the area during insertion of the trial into the intervertebral space along the medial lateral plane. The window and post configuration of head portion 340, thus allows the surgeon to accurately determine the center of the trial head portion and allows the surgeon to make positioning adjustments. As one of skill in the art would understand, the configuration of the window, including its size and dimensions, allow for the center post to be seen during imaging from a variety of angles, particularly considering that the approach to the intervertebral space is oblique. Furthermore, imaging along the anterior-posterior plane will similarly reveal the center of head portion 340 and allow a surgeon to make positioning adjustments. As further seen, and discussed in more detail below, the upper and lower surfaces of head portion 340 contain channels 346 and 348, which serve as keyed recesses for the chisel.

Figure 29:
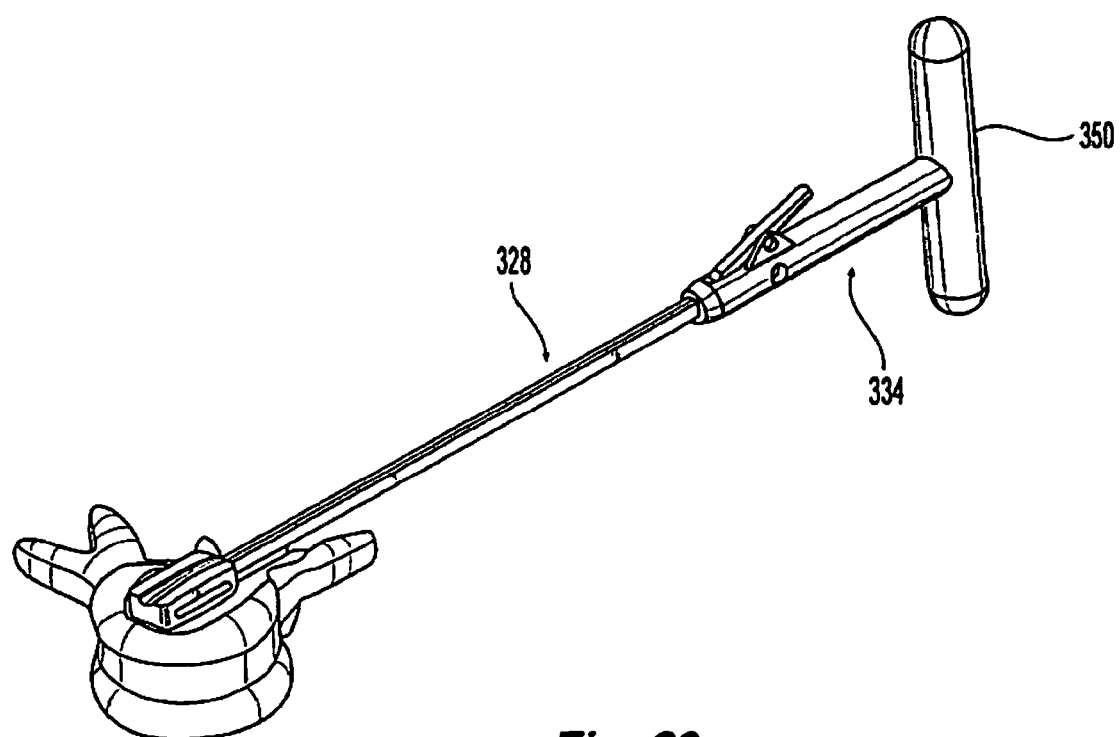
FIG. 29 is a perspective view of a trial according to an embodiment of the present invention.
Figure 30:
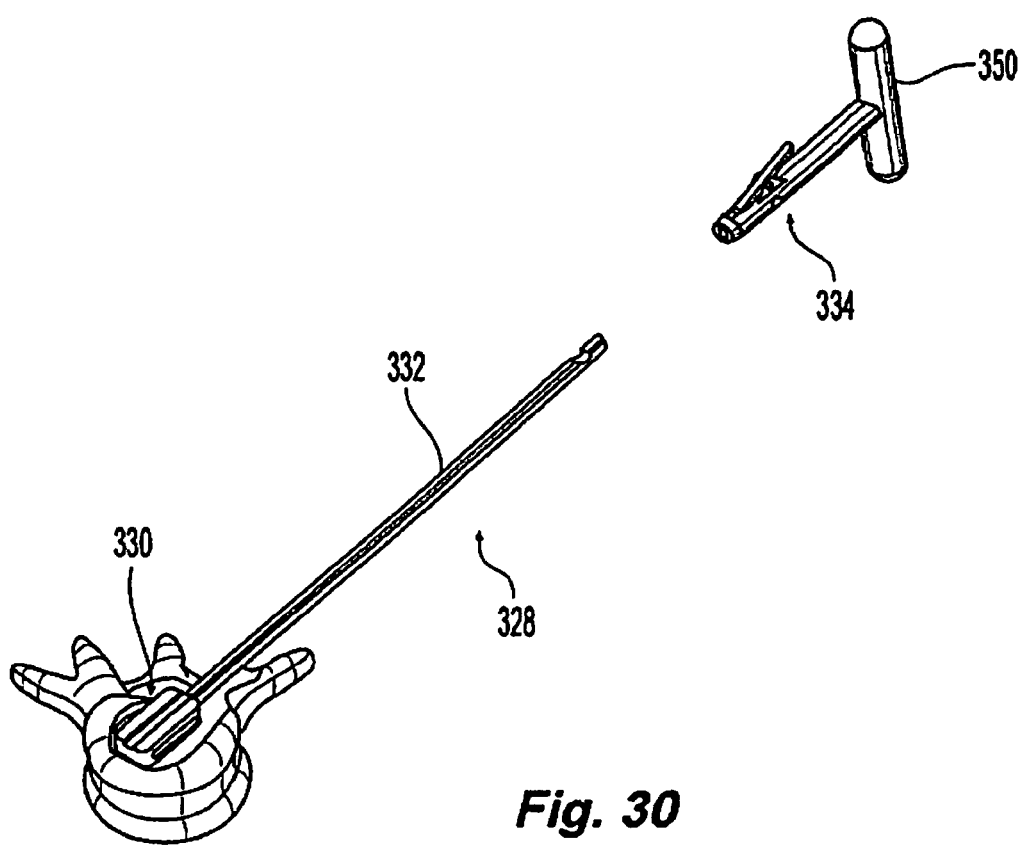
FIG. 30 is a perspective view of a trial according to an embodiment of the present invention.

With reference to FIG. 29, after preparation of the vertebral bodies, a surgeon may insert trial 328 into the intervertebral space. As seen in FIG. 29, handle portion 334 of trial 328 may be configured with flat face 350. Accordingly, a surgeon may strike flat face 350 with another tool to insert trial 328 to the desired depth. As discussed previously, a variety of positioning aids may be formed on the trial, and more particularly the head portion of the trial to aid the surgeon in positioning the trial. Once trial 328 has been inserted and positioned by the surgeon, the surgeon may release handle portion 334 of trial 328. As seen in FIG. 30, this leaves head portion 330 and shaft portion 332 of trial 328 inserted in the intervertebral space.

Figure 31:
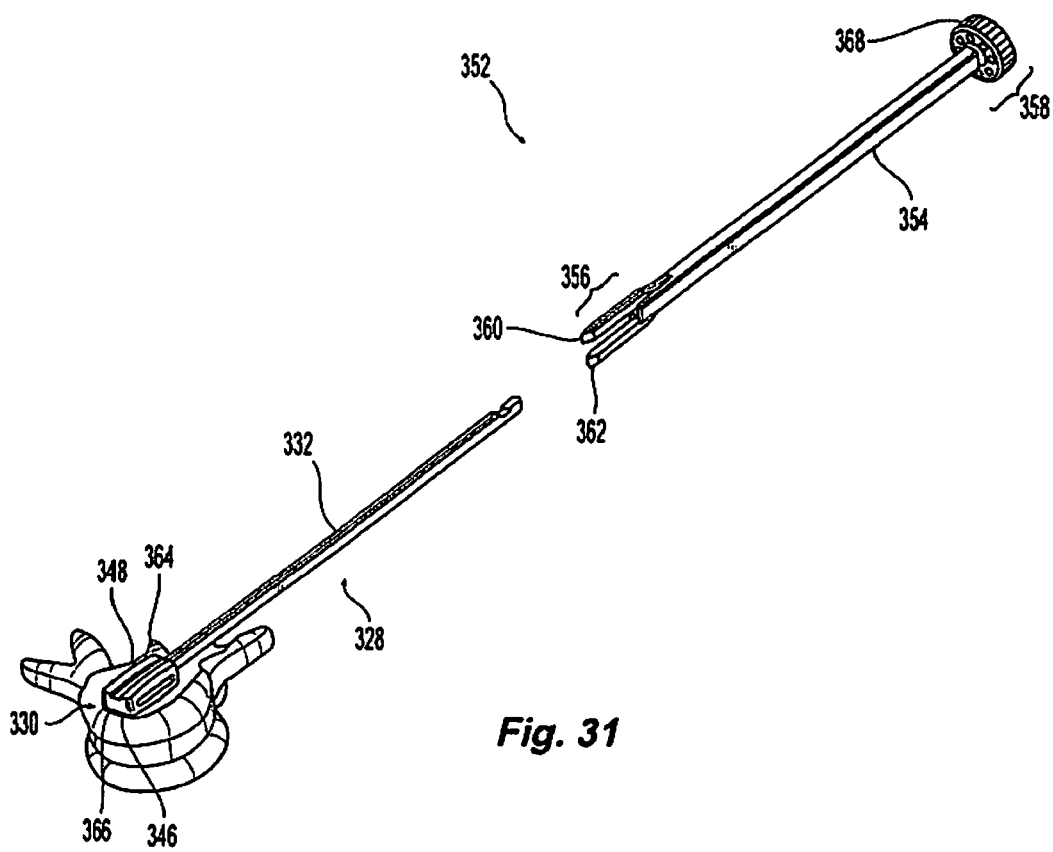
FIGS. 31-32 is a perspective view of a trial and chisel according to an embodiment of the present invention.

After removal of handle portion 334, a surgeon may then insert a chisel. With reference to FIG. 31, chisel 352 is an elongated hollow tubular shaft 354 with a blade portion 356 and end portion 358. Blade portion has a first blade 360 and second blade 362 that are sized and dimensioned to cut paths into the upper and lower surfaces of the intervertebral space. Chisel 352 fits over shaft 332 of trial 328. As one of skill in the art would understand, in an embodiment the shaft and chisel are shaped such that chisel 352 is keyed onto shaft 332. Accordingly, in such instances, shaft 332 may have a rectangular shape and the interior elongated shaft 354 of chisel 352 will have a substantially similar shape.

As seen in FIG. 31, blade portion 356 has two individual blades 360 and 362 connected to shaft 354 of chisel 352. Blades 360 and 362 are shaped and dimensioned to cut pathways into the upper and lower vertebral bodies to receive the keels of the prosthetic disc assembly being inserted. As further seen in FIG. 31, head portion 330 of trial 328 may be formed with an upper channel 348 and lower channel 346 in upper surface 364 and lower surface 366, respectively, of the head portion 330. Upper and lower channels 348 and 346 are configured to receive blades 360 and 362. In this fashion, the blades are directed along a particular path and the location of the pathways formed in the upper and lower surfaces of the intervertebral space are determined by the position of the trial head, which in turn is controlled by the surgeon.

Figure 32:
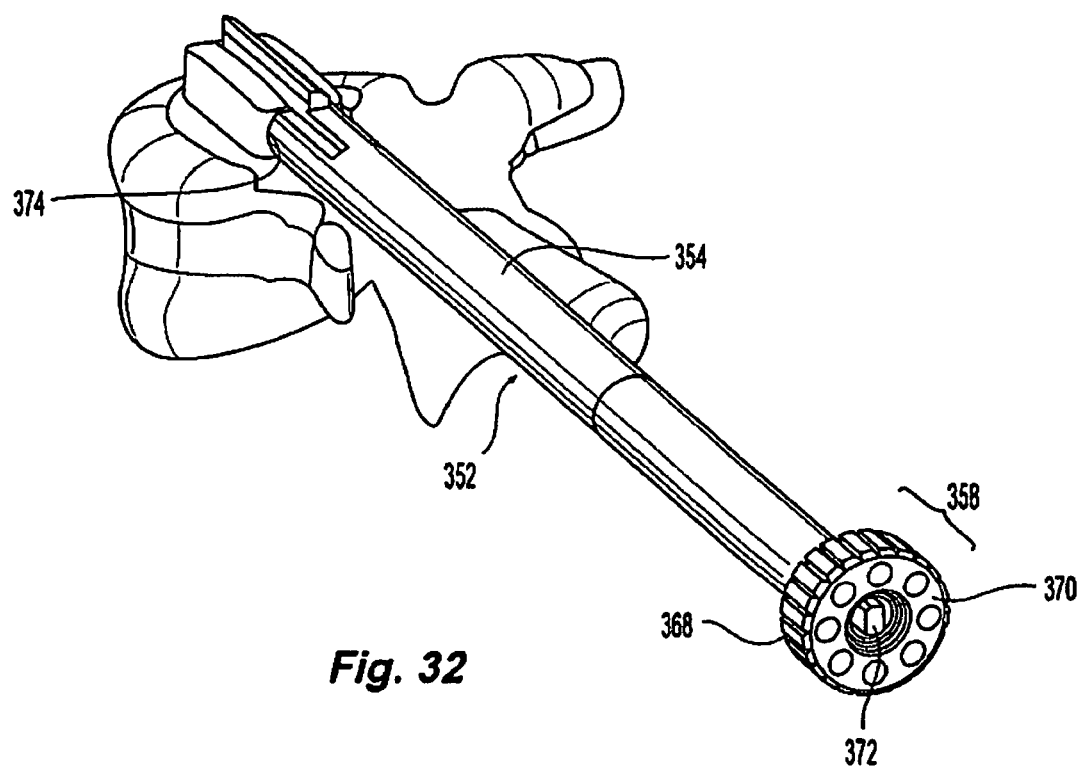

As seen in FIG. 31, end portion 358 of chisel 352 is configured with a circular portion 368, which is configured for a surgeon to grasp. With reference to FIG. 32, end portion 358 is also hollow. End portion 358 may be configured with a flat face 370, which provides a strike surface for a surgeon. Accordingly, a surgeon may use an instrument to strike flat face 370 of chisel 352 and drive the chisel into the intervertebral space. In an embodiment of the invention, the overall length of chisel 352 is configured such that upon full insertion of chisel 352 over trial 328 and into the intervertebral space, end portion 372 of shaft 354 is aligned with flat face 370. Thus, the two surfaces act as a stop or reference that the surgeon may use as an indication that the chisel has been fully inserted. In conjunction with this feature, the shaft may also be configured to provide a stop. As seen in FIG. 32, end 374 of chisel 352 is configured to abut or contact head portion 330 of trial 328. This contact may further act as a stop or indication that the chisel has been fully inserted into the intervertebral space.

Figure 33:
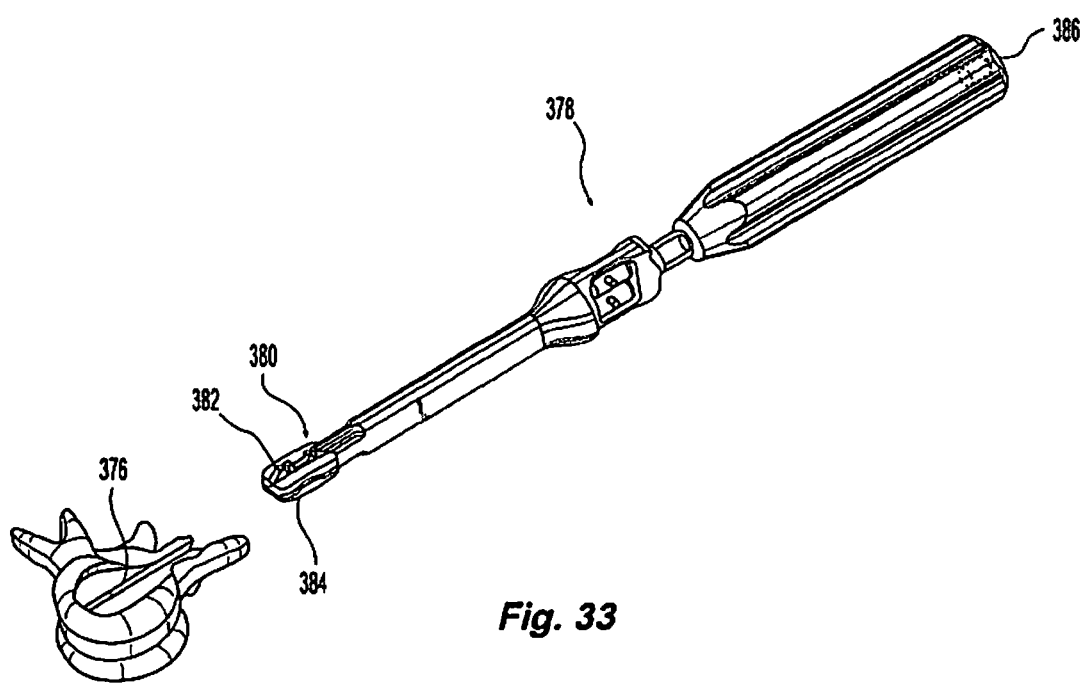
FIGS. 33-34 are perspective views of an implant and implant holder according to an embodiment of the present invention.

As seen in FIG. 32, the chisel has been fully inserted into the intervertebral space. Accordingly, pathways have been cut in both the upper and lower surfaces of the intervertebral space. With reference to FIG. 33, chisel 352 and trial 328 have been removed. As seen in FIG. 33, pathway 376 is shown cut into the lower vertebral body. For the sake of clarity, the upper vertebral body is not shown although one of skill in the art would understand that a similar pathway is cut by the chisel in the lower surface of the upper vertebral body.

After removal of the chisel and trial, a surgeon may then insert the prosthetic disc assembly. As seen in FIG. 33, prosthetic disc assembly is releasably attached to implant holder 378. A surgeon may then use implant holder to insert prosthetic disc 380 into the intervertebral space. As one of skill in the art would understand, keels 382,384 are aligned with the pathways cut into the upper and lower surfaces of the intervertebral space. Once aligned, a surgeon may then drive the prosthetic disc into the intervertebral space. Implant holder may be designed with flat face 386 to provide the surgeon with a strike surface to help drive the implant into the intervertebral space.

Figure 34:
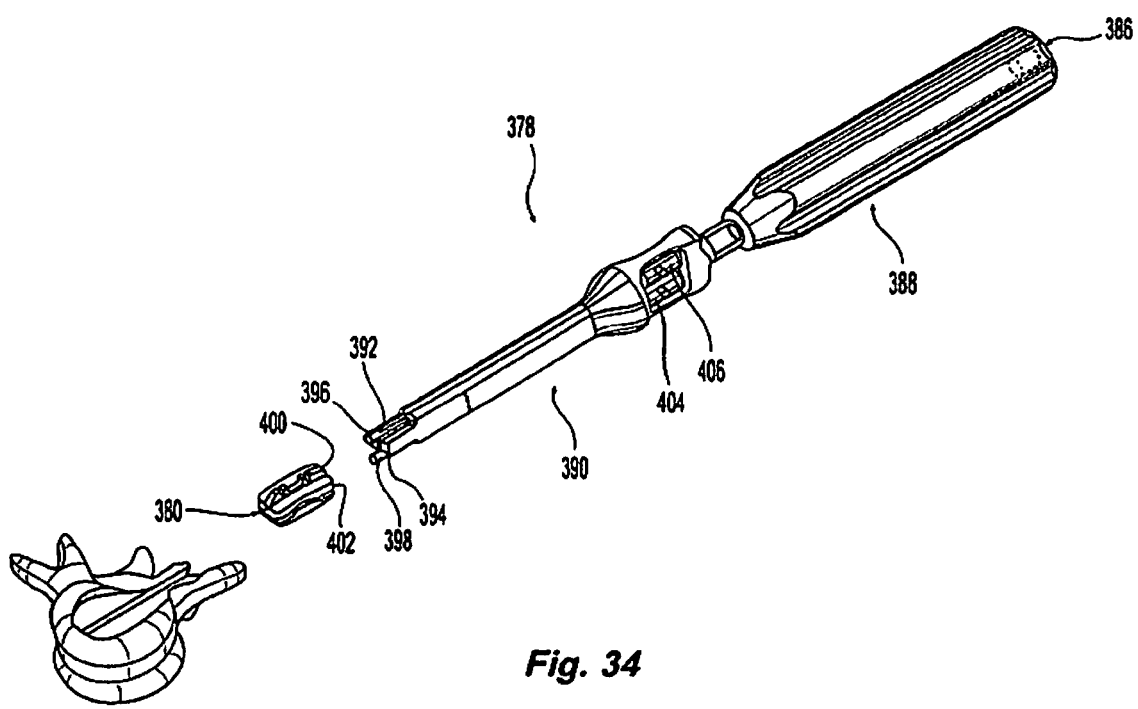

With reference to FIG. 34, implant 380 may be released from implant holder 378. While the method contemplates releasing the implant after it has been inserted, FIG. 34 shows an exploded view for the sake of clarity. Once the implant is inserted, however, the surgeon may image the treated area to determine the position of the prosthetic disc. The prosthetic disc assembly may have positioning aids to help a surgeon determine whether the disc is in the proper position within the intervertebral space As seen in FIG. 34, implant holder 378 has a handle portion 388 and shaft portion 390. Handle portion 388 is designed for a surgeon to grasp and as discussed previously may be configured with flat face 386. Shaft portion 390 houses two elongate rods 392, 394 that extend generally the length of shaft portion 390. Rods 392,394 have threaded ends that may extend beyond shaft 390. Threaded ends 396, 398 are designed to engage interiorly threaded bore holes 400,402 that reside on prosthetic disc 380. In this fashion, prosthetic disc 380 may be releasably attached to implant holder 378. Each rod 392,394 of shall 390 may be attached to a wheel. As seen in FIG. 34, wheels 404,406 are attached to rods 394, 392, respectively. Accordingly, as wheels 404, 406 are rotated so are rods 394,392. In this fashion, a surgeon may actuate the elongate rods and their respective threaded ends to engage the interiorly threaded bore holes on the prosthetic disc.

Figure 35:
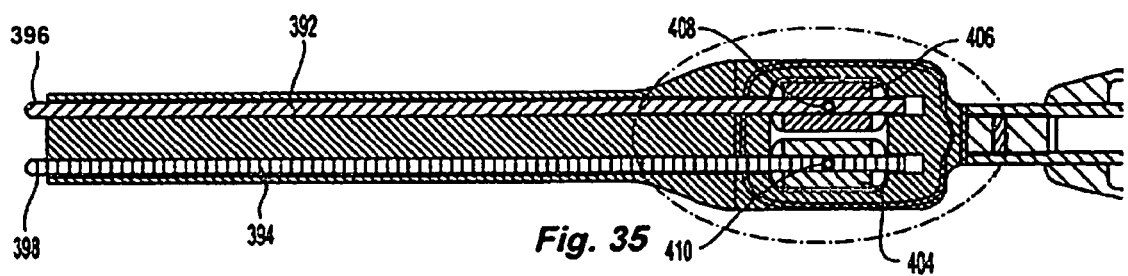
FIGS. 35-36 are cross sectional views of an implant holder according to an embodiment of the present invention.
Figure 36:
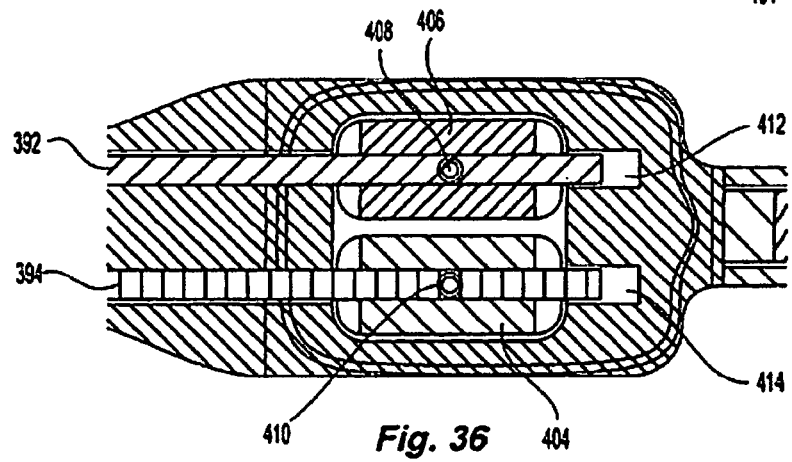
Figure 37:
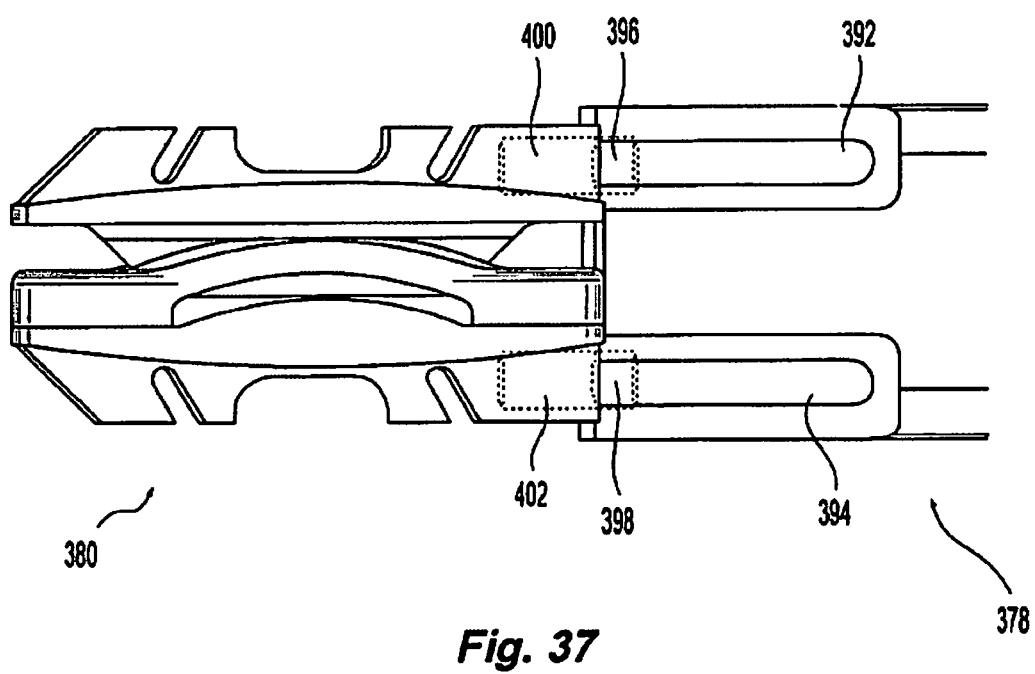
FIGS. 37-38 are perspective views of an implant according to an embodiment of the present invention.

With reference to FIG. 35, part of implant holder 378 is shown in a cross section view. As seen if FIG. 35, wheels 404,406 may be attached to rods 392,394 by screws 408, 410. With reference to FIG. 36, elongate rods 392,394 may extend into shaft portion 390, but shaft portion 390 is configured to leave spaces 412,414. This configuration allows rods 392, 394 to translate by a small amount, which improves the threading engagement of threaded ends 396, 398 onto bore holes of the prosthetic disc. Because each rod 392,394 is allowed to translate independent of the other, threaded engagement of threaded ends 396,398 into bore holes 400,402 is improved. In alternative embodiments, springs may be provided to tension rods 392, 394. In this fashion, threaded ends 396,398 are tensioned, which eases engagement of the rods when the prosthetic disc is seated to the implant holder. As one of skill in the art would understand, independent tensioning of the rods allows a user to seat the prosthetic disc assembly to the implant holder and then engage each rod to the implant's threaded bores. With reference to FIG. 37, implant holder 378 is shown attached to prosthetic disc 380. As seen in FIG. 37, threaded ends 396, 398 of rods 392, 394 are shown engaging bore holes 400,402. As one of skill in the art would understand, any number of different mechanisms may be employed to attach the implant to the implant holder.

Figure 38:
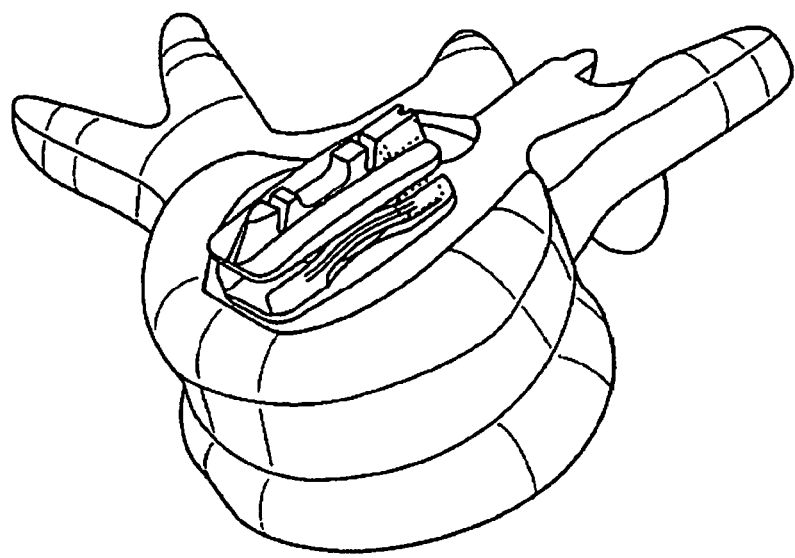

With reference to FIG. 38, the prosthetic disc is shown inserted into the intervertebral space in its final position. As seen in FIG. 38, the prosthetic disc is placed into the intervertebral space via a transforaminal approach, i.e. at an angle oblique to the medial-lateral axis. Accordingly, the methods and apparatus presented herein allow a surgeon to insert prosthetic discs into the intervertebral space via a transforaminal approach, for example. The prosthetic discs may also be implanted via anterior, anterior-lateral, lateral, or other suitable implantation approaches.

Figure 39A:
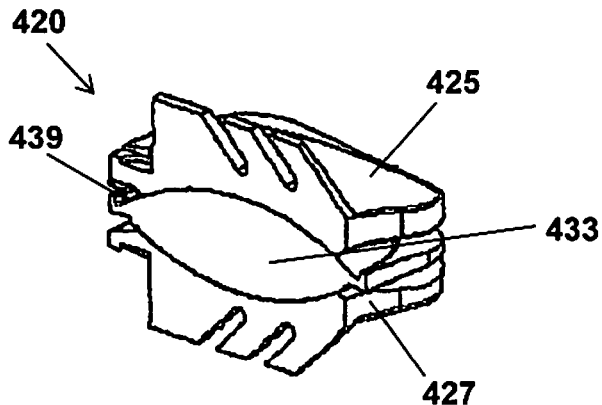
FIGS. 39a-c show views of a three-component implant including a core member between the two endplates.
Figure 39B:
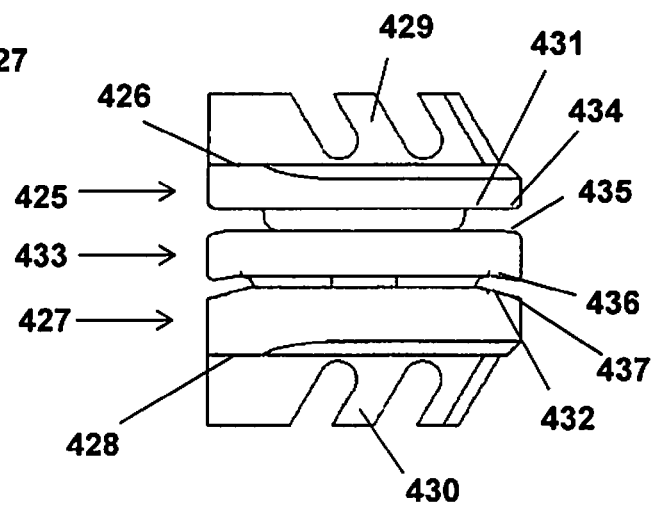
Figure 39C:
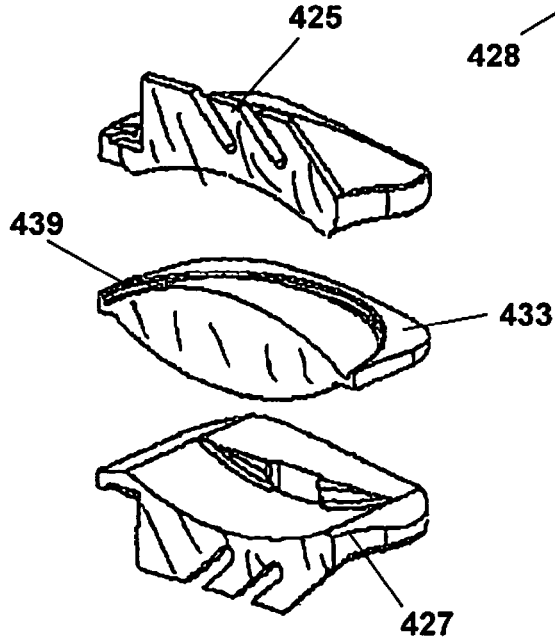

FIGS. 39a-39c show one example of a three component prosthetic disc 420. FIG. 39b is a side view of the prosthetic spinal disc 420 which may be located between sequentially aligned vertebral bodies, such as are found in the cervical, thoracic, and lumbar spine. Prosthetic spinal disc 420 conforms in size and shape with the spinal disc that it replaces and restores disc height and the natural curvature of the spine. Prosthetic spinal disc 420 comprises two opposite endplate 425 and 427 which are disposed in two substantially parallel horizontal planes when it is at rest, i.e., when it is not subjected to any load, either moderate or heavy.

Outer faces 426 and 428 of endplates 425 and 427 are in direct contact with vertebral bodies (not shown) and may be textured or have a plurality of teeth to ensure sufficient contact and anchoring to the vertebral bodies. Outer faces 426 and 428 of endplates 425 and 427 may also have a porous or macrotexture surface that facilitates bone ongrowth/ingrowth so that the prosthetic spinal disc 420 is firmly affixed to vertebral bodies. Outer faces 426 and 428 of endplates 425 and 427 may also have keels 429 and 430 that may fit into channels in the vertebral bodies to facilitate anchoring. Disposed between the inner faces 431, 432 of endplates 425 and 427 is a core 433, which is securely placed between the inner faces 431, 432 of endplates 425 and 427. A stop member is formed around the equator of the core 433, which functions to limit the motion of vertebral bodies beyond a predetermined limit that is deemed unsafe to the patient.

As shown in FIG. 39b, mechanical stops may be designed as part of the upper and lower endplates 425 and 427 and core 433. In this embodiment, the mechanical stop results as a function of the design of the upper and lower endplates 425 and 427 and the design of the core 433. For example and with continuing reference to FIG. 39b, upper endplate 425 is designed with a first contact surface 434 on the interior surface 431 of the upper endplate 425. Core 433 is designed with a second upper contact surface 435. During flexion and/or extension, first contact surface 434 may abut or come into contact with second contact surface 435, thus effectively limiting the degree of movement allowed by the articulating surfaces. Similarly, the core 433 is designed with a lower third contact surface 436 while lower endplate 427 is configured with an upper fourth contact surface 437. During extension and/or flexion, third contact surface 436 may abut or come into contact with fourth contact surface 437, thus effectively limiting the degree of movement allowed by the articulating surfaces. Contact surfaces 434, 435, 436, and 437 may be formed with various slopes, angled surfaces, and thickness to specify the degree of movement permitted by the disc design.

In an alternative embodiment, the stop member may be formed from a ridge of material disposed about the partially spherical surface of the core above the equatorial plane of core 433. As seen in FIGS. 39a and 39c, a cross sectional view and an exploded cross sectional view of the prosthetic disc 420 is shown. Prosthetic disc 420 has upper endplate 425, lower endplate 427 and core member 433 disposed there between. As seen in FIGS. 39a and 39c, core member 433 is formed with a lip or rim 439 that serves as a stop member. As endplate 425 moves relative to core 433 in response to movement of the spine, stop member 439 may approach or engage with endplate 425 to restrict further motion in a particular direction. Endplate 425 may be configured with a raised edge that mates or abuts with the stop member 439 of core member 433. Stop member 439 may be formed of a relatively rigid material so that additional motion is substantially prevented once engaged against an endplate. Alternatively, the stop material may be made of resilient material that provides some cushioning or flex from deformation of the stop material before the range of motion is fully limited.

In alternative embodiments, stop member 439 may be disposed on one or more of endplates 425 and 427. For instance, endplates 425 and 427 may be configured with raised areas or ridges on its perimeter that engage with either core 433 or an opposing endplate in order to limit further motion in a particular direction. Any of the stop members discussed above may be designed to limit motion to a greater degree in one direction than in another. Thus, the stop member may have various shapes and thicknesses to provide a variable range of motion that favors or disfavors movement in particular planes. For example, the stop member may have increased thickness on the side portion of the core to provide a more limited range of lateral motion of the spine while still allowing motion in the posterior/anterior direction.

The motion segment comprises an anterior prosthetic spinal disc 420 and adjacent upper and lower vertebral bodies. The exact contours of core 433, inner surfaces of endplates 425 and 427 and stop member 439 determine the range of motion allowed in flexion and extension, side bending, shear and rotation.

It is preferred that anterior prosthetic spinal disc 420 closely mimics the mechanical functioning and the various physical attributes of the natural spinal disc that it replaces. In some instances, however, the prosthetic spinal disc may permit a more limited range of motion in one or more directions in order to prevent further spinal injury. In general, the prosthetic spinal disc can help maintain the proper intervertebral spacing, allow for proper range of motion, and provide greater stability. It can also help transmit physiological stress more accurately.

Endplates 425 and 427, core 433, and stop 439 may be composed of a variety of biocompatible materials, including metals, ceramic materials and polymers. Such materials include, but are not limited to, aluminum, cobalt-chromium, alloys, and polyethylene. Outer surfaces 426 and 428 of the endplates 425 and 427 may also contain a plurality of teeth, maybe coated with an osteoconductive material, antibiotics or other medicament, or may have a porous or macrotexture surface to help rigidly attach the end plates to the vertebral bodies by promoting the formation of new bony ongrowth/ingrowth. Such materials and features may be used in any of the anterior prosthetic spinal discs described herein.

Similar to the prosthetic disc shown in FIG. 16, FIGS. 40-43 depict prosthetic disc 500 having two separate and distinct connection features suitable for implanting and removing the disc 500 from the disc space. As shown in the perspective view of FIG. 40, the prosthetic disc 500 has a first upper endplate 510 and a second bottom endplate 520. The first endplate 510 has a first outer surface 512 configured to substantially engage with a first vertebral body (not shown) and a second inner surface 514 comprising an articulating surface configured to allow for relative movement of the first endplate 510. The second endplate 520 has a first outer surface 522 configured to substantially engage with a second vertebral body (not shown) and a second inner surface 524 comprising an articulating surface configured to allow for relative movement of the second endplate 520.

The prosthetic disc 500 may be provided with or without keels as described above. For example, as shown in the cross-sectional view of FIG. 41, the first outer surface 512 of the first endplate 510 may have a first keel 505 extending therefrom configured to engage with a groove in the first vertebral body. Similarly, the first surface 522 of the second endplate 520 may have a second keel 506 extending therefrom configured to engage with a groove in the second vertebral body. As shown in FIG. 42, the first and/or second keels 505, 506 may have one or more slots 508 extending a length downwardly from a distal edge of the keel 505, 506 to the base of the keel 505, 506.

Figure 40:
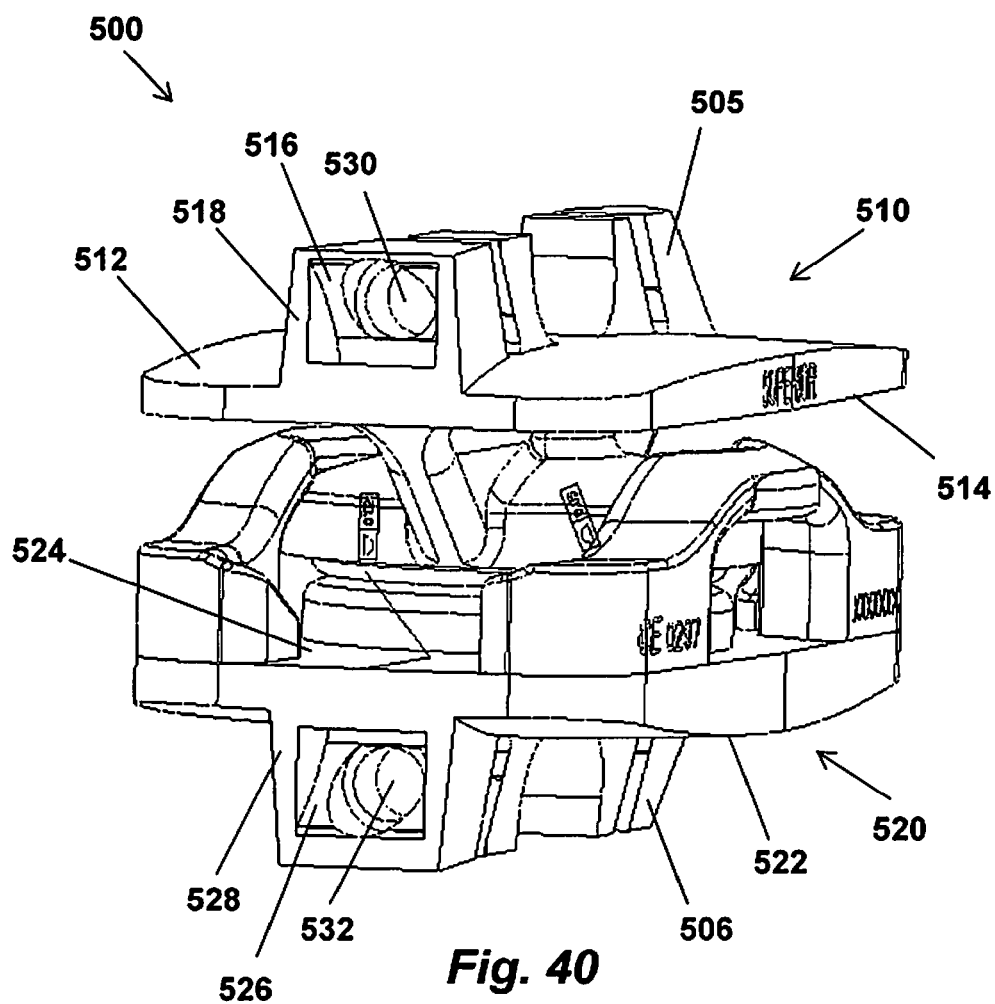
FIGS. 40-43 provide alternative views of an implant including optimized quick connect and threaded retaining features.
Figure 41:
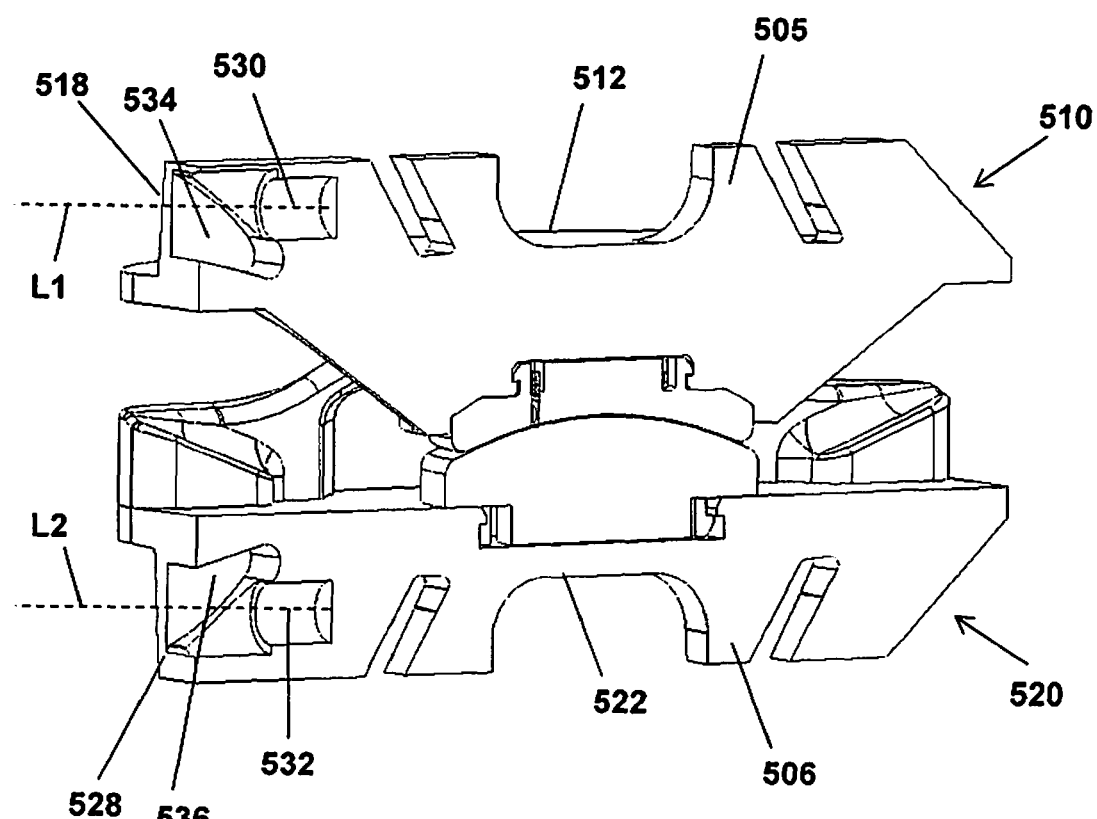
Figure 42:
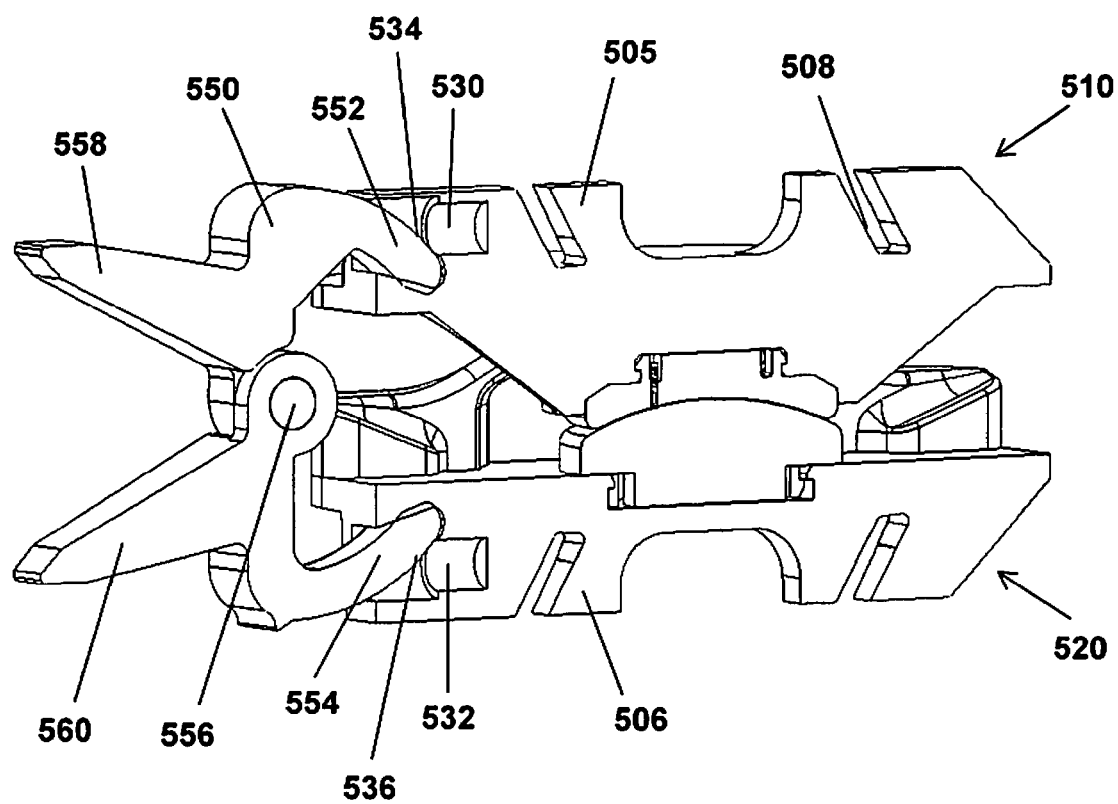

With reference to FIGS. 40 and 41, the first keel 505 may include a first trailing surface 518 opposite to the insertion end of the keel 505 with a first opening 516 extending therethrough. The first opening 516 includes at least two different areas for connecting the first endplate 510 of the disc 500 to one or more implant holding devices. For example, the first opening 516 may include a first bore hole 530 having a first longitudinal center axis L1. The bore 530 may be substantially cylindrical in shape and may extend a distance into the keel 505. The bore 530 may be in the form of a blind hole, i.e. where the bore 530 does not extend through the keel 505. The bore 530 may be threaded to provide for a threaded connection to a threaded holder. The first opening 516 may also include a first curved cutout 534 having a curvature extending inward toward the first inner surface 514 and away from the first outer surface 512 of the first endplate 510. The first curved cutout 534 may extend a distance into the keel 505. The first curved cutout 534 may also be in the form of a blind hole, i.e. where the first curved cutout 534 does not extend through the keel 505. The first curved cutout 534 extends obliquely relative to the first longitudinal axis L1 of the bore hole 530. The oblique projection of the first curved cutout 534 is intended to include an orientation that is neither parallel nor perpendicular to the first longitudinal axis L1 of the bore hole 530.

With continued reference to FIGS. 40 and 41, the second keel 506 may have a second trailing surface 528 opposite to the insertion end of the keel 505 with a second opening 526 extending therethrough. The second opening 526 may also include at least two different areas for connecting the second endplate 520 of the disc 500 to one or more implant holding devices.

For example, the second opening 526 includes a second bore hole 532 having a second longitudinal center axis L2. The bore 532 may be substantially cylindrical in shape and may extend a distance into the keel 506. The bore 532 may be in the form of a blind hole, i.e. where the bore 532 does not extend through the keel 506. The bore 532 may be threaded to provide for a threaded connection to a threaded holder. The second opening 526 may also include a second curved cutout 536 having a curvature extending inward toward the first inner surface 524 and away from the first outer surface 522 of the second endplate 520. The second curved cutout 536 may extend a distance into the keel 506. The second curved cutout 536 may also be in the form of a blind hole, i.e. where the second curved cutout 536 does not extend through the keel 506. The second curved cutout 536 may extend obliquely from the second longitudinal axis L2 of the second bore hole 532.

Although the first and second retaining features including the first and second bores 530, 532 and first and second curved cutouts 534, 536 are described and shown in the keels 505, 506, it is contemplated that the retaining features may be positioned at any other suitable location or locations on the first and second endplates 510, 520. The first and second curved cutouts 534, 536 and the first and second bore holes 530, 532 act as connection points for one or more implant holders. In particular, the first and second curved cutouts 534, 536 are configured to receive a first retaining feature and the first and second bore holes 530, 532 are configured to receive a second retaining feature. These connection features allows for the disc 500 to be secured with either a quick connection or a threaded connection through one continuous feature.

As shown in the cross sectional view of FIG. 42, the first retaining feature may engage a quick connect holder 550 having a first arm portion 552 configured to engage the first curved cutout 534 in the first endplate 510 and a second arm portion 554 configured to engage the second curved cutout 536 in the second endplate 520. The first and second arm portions 552, 554 may be coupled together at a pivot point 556 (e.g., a pin or the like), which allows the first and second arm portions 552, 554 to rotate in an arc toward and away from one another. The first and second arm portions 552, 554 may each include a rounded or curved distal end configured to mate with the first and second curved cutouts 532, 534 in the endplates 510, 520. The first and second arm portions 552, 554 may be connected to first and second handle portions 558, 560, respectively. The first and second handle portions 558, 556 may extend to form the handles of the instrument or may attach to other components designed to move the first and second arms portions 552, 554. Thus, the operator may easily compress the first and second arm portions 552, 554 together to grasp the first and second endplates 510, 520 of the disc 500 in a quick connect manner. Similarly, the first and second arm portions 552, 554 may be easily extended away from one another to release the disc 500 after implantation. Thus, the quick connect connections including the first and second curved cutouts 534, 536 and holder 550 may provide for a non-threaded, straight-forward, and simple attachment mechanism designed to aid in simple implantation of the disc 500.

Figure 43:
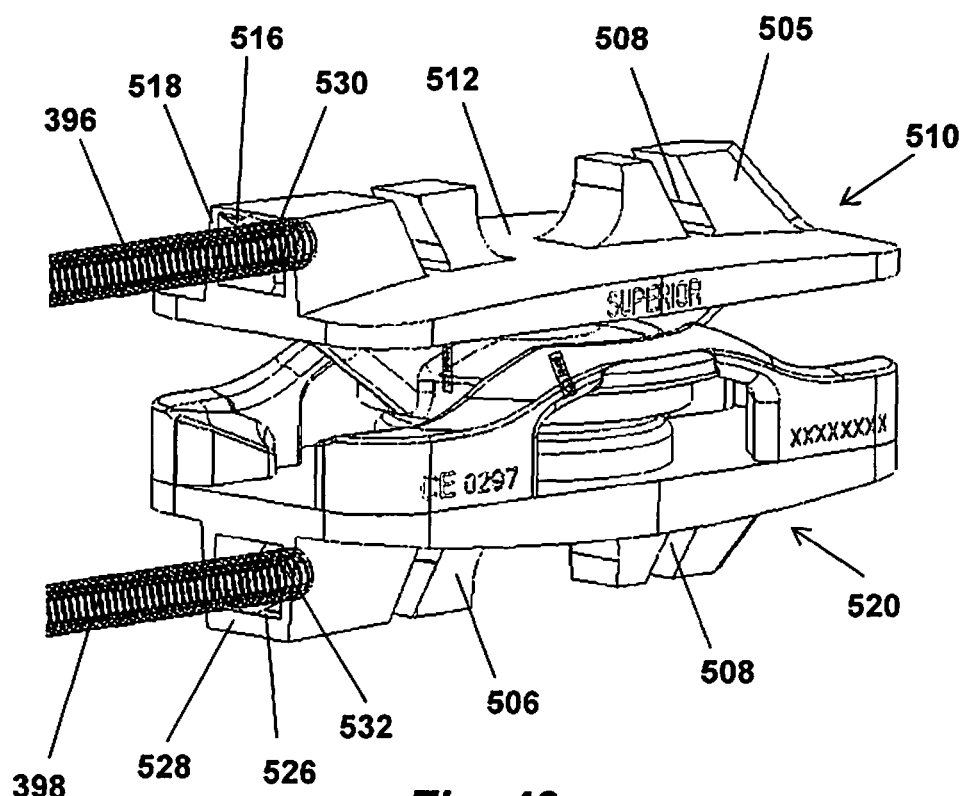

As shown in the perspective view of FIG. 43, the first and second bore holes 530, 532 may be threaded such that the second retaining feature is a threaded holder. The threaded holder may include holder 378 described above and shown in FIGS. 33-37. For example, the threaded ends 396, 398 may be sized and configured to engage the threaded bore holes 530, 532, respectively. Although holder 378 is exemplified, any suitable threaded holder may be used. The threaded holder and connections may provide for a secure connection to assist in removal of the disc 500. In particular, the threaded connection may be particularly helpful in instances where the endplates 510, 520 have shifted from the insertion orientation and are unaligned, which may prevent the quick connect or other standard holder from being used.

Thus, the continuous internal features allow for two different types of connections to the disc 500 through a single opening 516, 526 in each of the first and second endplates 510, 520. These internal features avoid having to use significantly more material volume, external surface area, or needing to use a different space or area for a second tool attachment point. Utilizing two connection features in a single opening 516, 526 improves the efficiency of how the internal area is used, thereby leading to improved mechanical characteristics of the disc 500. Although these connection features are depicted with reference to disc 500, it is contemplated that the dual retaining features may be applied to any of the prosthetic discs described herein or hereafter contemplated.

Figure 44:
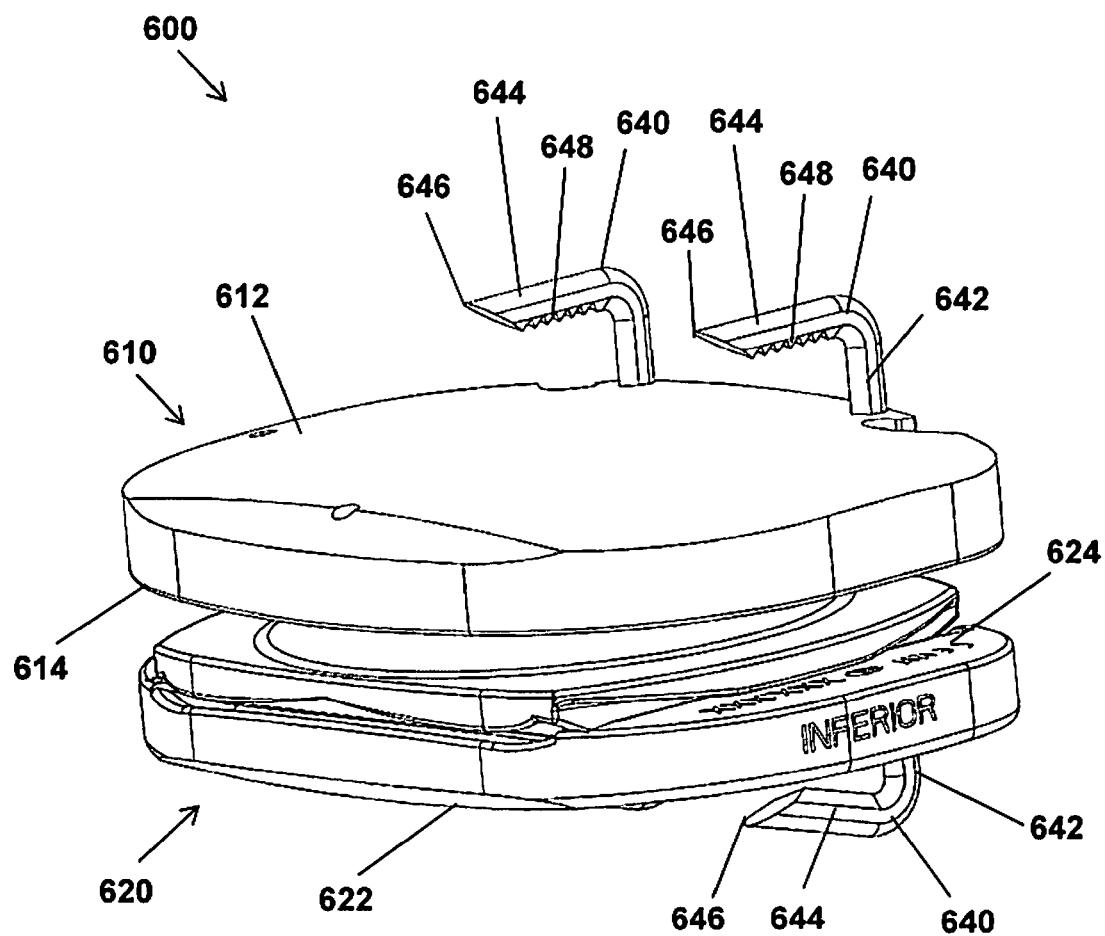
FIGS. 44-46 show alternative views of an implant including pins or spikes designed to provide primary and secondary stability after implantation.
Figure 45A:
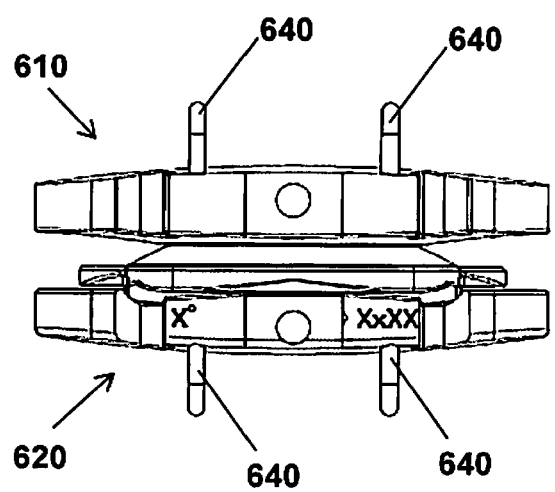
Figure 45B:
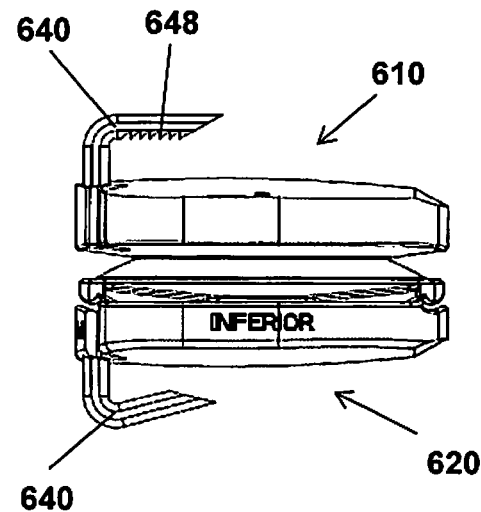
Figure 45C:
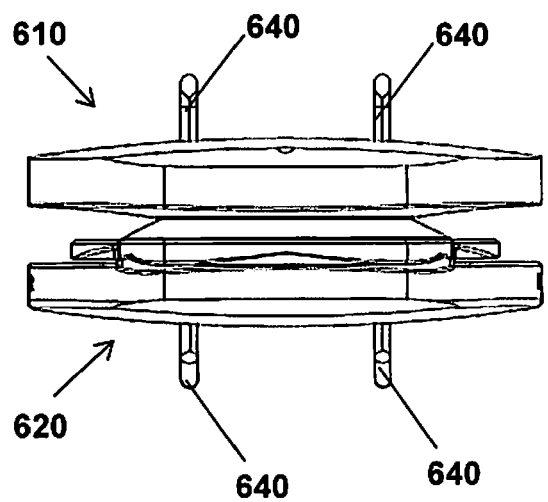
Figure 45D:
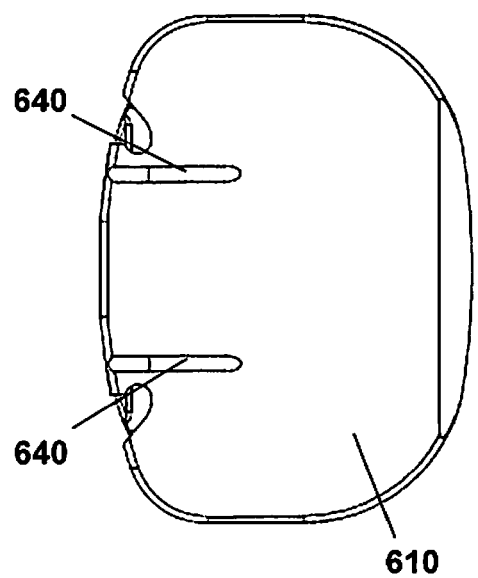
Figure 46:
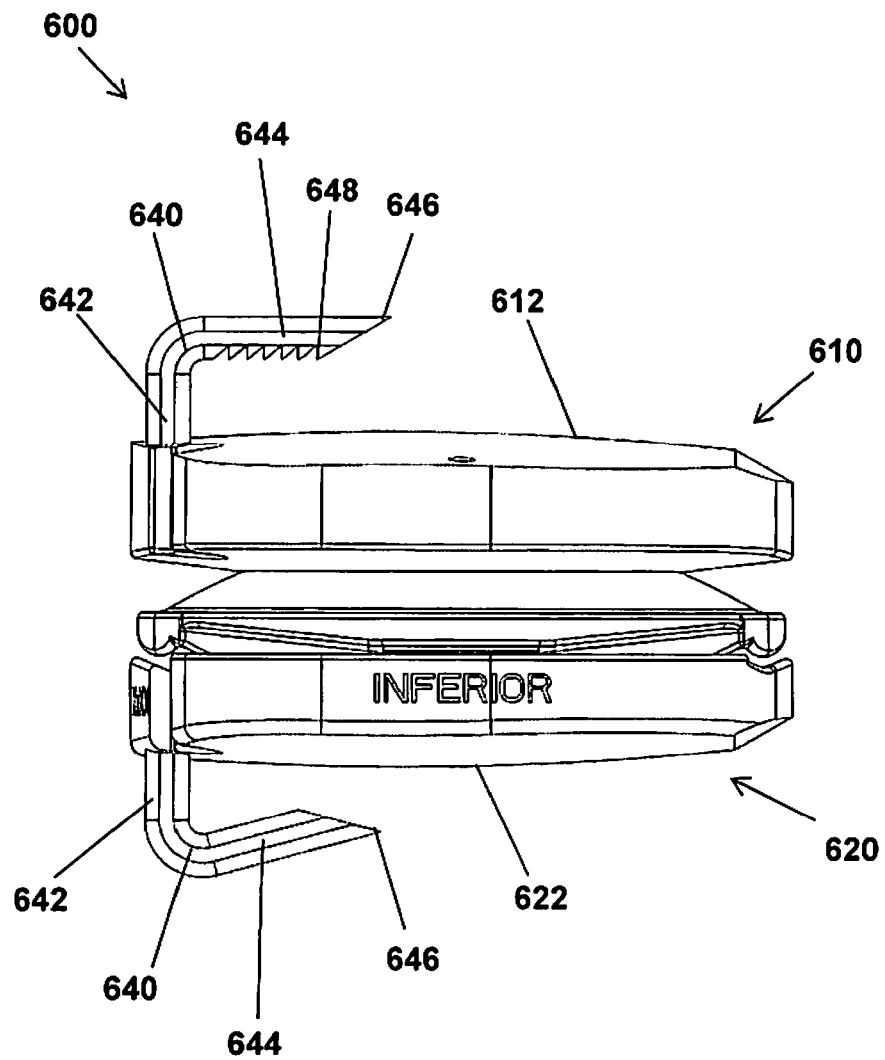

As shown in FIGS. 44-46, an intervertebral prosthetic disc 600 includes a first upper endplate 610 and a second bottom endplate 620 having at least one stability feature. The stability feature imparts primary stability to hold the disc 600 in place while bone grows into the vertebral endplates and provides a secondary stability over time without the need for a keel.

As shown in the perspective view of FIG. 44, the first endplate 610 has a first upper surface 612 configured to substantially engage with a first vertebral body (not shown) and a second inner surface 614 comprising an articulating surface configured to allow for relative movement of the first endplate 610. The second endplate 620 has a first outer surface 622 configured to substantially engage with a second vertebral body (not shown) and a second inner surface 624 comprising an articulating surface configured to allow for relative movement of the second endplate 620.

With continued reference to FIG. 44, the first surfaces 612, 622 of the first and second endplates 610, 620 may be smooth without keels or the like. By removing the keels and eliminating the need for cutting an opening in the vertebral endplate to receive a keel and by leaving the vertebral endplate intact, the chances of fracturing the vertebral endplate is reduced, and the possibility of additional bleeding on the vertebral endplates due to extensive preparation is reduced. Removing the keels also eliminates the need to have high speed mills to prepare the vertebral endplates, which adds to surgical time and complexity. Although depicted without keels, it is contemplated that keels may be used in addition to the one or more stability features.

The stability feature may include at least one stabilizing body 640. The stabilizing body 640 may be in the form of one or more pins or spikes attached to the first and/or second endplates 610, 620. For example, the stabilizing body 640 may take the form of a wire, hollow cylinder, flat bar, spiral, helical shape, or the like. The stabilizing body 640 may also have any suitable cross sectional shape including circular, elliptical, square, rectangular, etc.

The stabilizing body 640 is attached or affixed to either or both of the first and second endplates 610, 620. The stabilizing body 640 may be attached using any suitable techniques and methods known in the art. For example, a friction fit, dowel pins, hooks, staples, screws, adhesives, or the like, or any suitable fasteners known in the art can be used to permanently attach the stabilizing body 640 to the endplate 610, 620. In addition, any suitable number and configuration of stabilizing bodies 640 may be attached to the first and second endplates 610, 620. With reference to FIG. 45a showing a rear view, FIG. 45b showing a side view, FIG. 45c showing an insertion end view, and FIG. 45d showing a top view of one embodiment, two stabilizing bodies 640 may be affixed to the rear portion of the first endplate 610 to project upward and toward the insertion end of the first endplate 610. Similarly, two stabilizing bodies 640 may be affixed to the rear portion of the second endplate 610 to project downward and toward the insertion end of the second endplate 620. The two stabilizing bodies 640 may be positioned, for example, in increments of about one-third of the width of the disc 600. It is contemplated, however, that more or less stabilizing bodies 640 may be used and positioned at any suitable location along the first and second endplates 610, 620 to impart primary and second stability after implantation.

As shown in the side view of FIG. 46, the stabilizing body 640 may include a first elongated portion 642 having first and second ends, a second elongated portion 644 having first and second ends, the second end of the first elongated portion 642 and the first end of the second elongated portion 644 are integrally formed with each other to form a substantially L-shaped body. The first end of the first elongated portion 642 may be connected to the first or second endplate 610, 620 and the second end of the second elongated portion 644 is free to engage the first or second vertebral body. In particular, a distal end 646 of the second elongated portion 644 may be pointed or sharpened to ease insertion into the vertebrae.

The stabilizing body 640 may transition between one or more configurations. For example, the stabilizing body 640 may have a first, insertion configuration and a second, secured configuration. In the first configuration, the stabilizing body 640 may be configured to enhance ease of insertion of the stabilizing bodies 640 and endplates 610, 620 during implantation. In the second configuration, the stabilizing body 640 may be configured to compress on the vertebral endplates and permanently secure the disc 600 in the vertebral space.

In the first configuration (as shown in FIG. 46 for the stabilizing body 640 extending from the first upper endplate 610), the second elongated portion 644 of the stabilizing body 640 may be substantially perpendicular to the first elongated portion 642 and substantially parallel to the first endplate 610 to facilitate insertion of the prosthetic disc 600. Although only shown with respect to the first endplate 610, a similar configuration would be provided for the stabilizing body 640 extending from the second endplate 620. In particular, the second elongated portion 644 of the stabilizing body 640 may be substantially perpendicular to the first elongated portion 642 and substantially parallel to the second endplate 620, in the first configuration, to facilitate insertion of the prosthetic disc 600.

In the second configuration (as shown in FIG. 46 for the stabilizing body 640 extending from the second lower endplate 620), the second elongated portion 644 may be compressed closer to the first surface 622 of the second endplate 620 to secure the prosthetic disc 600 to the vertebral body and provide the needed primary stability. For example, the second elongated portion 644 of the stabilizing body 640 may be substantially oblique relative to the first elongated portion 642 and the second endplate 620. Although only shown with respect to the second endplate 620, a similar configuration would be provided for the stabilizing body 640 extending from the first endplate 610. In particular, the second elongated portion 644 of the stabilizing body 640 may be substantially oblique relative to the first elongated portion 642 and the first endplate 610, in the second configuration, to hold the disc 600 in place and allow for bony in-growth. For example, in the second configuration, the second elongated portion 644 may be provided at an angle less than 90° relative to the first elongated portion 642. In particular, the second elongated portion 644 may be provided at an angle of about 45-80°, about 50-75°, or about 60-70° relative to the first elongated portion 642.

The stabilizing bodies 640 may also be provided with one or more teeth, spikes, or serrations 648 configured to prevent retropulsion of the disc 600 after implantation. For example, a portion of the second elongated portion 644 may be serrated to enhance stability of the stabilizing body 640 in the second, compressed configuration. The serrations 648 may be positioned on an underside of the stabilizing body 640 or a portion of the stabilizing body 640 proximate to the first and/or second endplates 610, 620. In addition, the serrations 648 may be oriented to allow for ease of insertion of the stabilizing bodies 640, but designed to resist removal. Although the serrations 648 are only depicted on the stabilizing bodies 640 shown extending from the first endplate 610, similar serrations 648 may also be provided on the stabilizing bodies 640 extending from the second endplate 620.

The transition between the first and second configurations may occur when the stabilizing body 640 is at least partially formed from a shape memory alloy, such as a temperature sensitive shape memory alloy. For example, the shape memory alloy may include a copper-aluminum-nickel alloy or a nickel-titanium alloy (i.e., Nitinol). Such memory alloys may have two natural shapes, one shape when at a lower temperature below the transition temperature and another shape when at a higher temperature above the transition temperature. The stabilizing bodies 640 may be at least partially or completely formed from a temperature sensitive shape memory alloy which has a transition temperature around, at, or below body temperature (e.g., about 37° C.). For example, the stabilizing body 640 may be in the first configuration when at a temperature below body temperature, then when the stabilizing body 640 reaches body temperature (i.e., after implantation) the stabilizing body transitions into the second configuration reverting to the pre-programmed shape to compress against the vertebral endplates, secure the disc 600, and provide primary and secondary stability. Although the stability features are depicted and described with reference to disc 600, it is contemplated that the stabilizing bodies 640 may be applied to any of the prosthetic discs described herein or hereafter contemplated.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments that fall within the true spirit and scope of the present invention.

What is claimed is:

1. An intervertebral prosthetic disc comprising:
a first endplate having a first surface configured to substantially engage with a first vertebral body and a second surface comprising an articulating surface configured to allow for relative movement of the first endplate; and
a second endplate having a first surface configured to substantially engage with a second vertebral body and a second surface comprising an articulating surface configured to allow for relative movement of the second endplate;
wherein the first surface of the first endplate has a first keel, the first keel having a first leading end opposite to a first trailing surface, a first outer side surface, and a second outer side surface, the first trailing surface defining a first opening extending therethrough, the first opening including a first bore hole having a first longitudinal axis extending from the first trailing surface toward the first leading end, and the first opening including a first curved cutout in the form of a blind hole extending toward the first or second outer side surfaces of the first keel, wherein the first curved cutout does not extend through the first keel,
wherein the first surface of the second endplate has a second keel, the second keel having a second leading end opposite to a second trailing surface, a first outer side surface, and a second outer side surface, the second trailing surface defining a second opening extending therethrough, the second opening including a second bore hole having a second longitudinal axis extending from the second trailing surface toward the second leading end, and the second opening including a second curved cutout in the form of a blind hole extending toward the first or second outer side surfaces of the second keel, wherein the second curved cutout does not extend through the second keel,
wherein the first and second curved cutouts are configured to receive a first retaining feature and the first and second bore holes are configured to receive a second retaining feature.

2. The intervertebral prosthetic disc of claim 1, wherein the first and second curved cutouts are configured to receive the first retaining feature in the form of a quick connect holder having a first arm configured to engage the first curved cutout and a second arm configured to engage the second curved cutout.

3. The intervertebral prosthetic disc of claim 2, wherein the first and second cutouts are configured to engage the first arm and the second arm coupled at a pivot point.

4. The intervertebral prosthetic disc of claim 1, wherein the first and second bore holes are threaded.

5. The intervertebral prosthetic disc of claim 4, wherein the first and second cutout are configured to receive the second retaining feature in the form of a threaded holder.

6. The intervertebral prosthetic disc of claim 1 further comprising a core element at least partially disposed between the first and second endplates.

7. The intervertebral prosthetic disc of claim 6, wherein the core element comprises a first contoured surface in communication with and substantially corresponding to the second surface of the first endplate, and a second contoured surface substantially in communication with and substantially corresponding to the second surface of the second endplate.

8. The intervertebral prosthetic disc of claim 7, wherein the articulating surface of the second endplate permits rotation of the second endplate relative to the core element substantially in the sagittal plane.

9. The intervertebral prosthetic disc of claim 7, wherein the articulating surface of the second surface of the first endplate permits rotation of the first endplate relative to the core element substantially in all planes.

10. The intervertebral prosthetic disc of claim 1, wherein the first and second endplates are constrained to prevent separation of the first and second endplates from each other.

11. An intervertebral prosthetic disc comprising:
a first endplate; and
a second endplate;
wherein the first endplate has a first keel having a first leading end opposite to a first trailing surface, a first outer side surface, and a second outer side surface, the first keel having a first bore hole having a first longitudinal axis extending from the first trailing surface toward the first leading end and a first curved cutout in the form of a blind hole extending toward the first or second outer side surfaces of the first keel, wherein the first curved cutout does not extend through the first keel,
wherein the second endplate has a second keel having a second leading end opposite to a second trailing surface, a first outer side surface, and a second outer side surface, the second keel having a second bore hole having a second longitudinal axis extending from the second trailing surface toward the second leading end and a second curved cutout in the form of a blind hole extending toward the first or second outer side surfaces of the second keel, wherein the second curved cutout does not extend through the second keel, wherein the first and second curved cutouts are configured to receive a first retaining feature and the first and second bore holes are configured to receive a second retaining feature.

12. The intervertebral prosthetic disc of claim 11, wherein the first and second curved cutouts are configured to receive the first retaining feature in the form of a quick connect holder having a first arm configured to engage the first curved cutout and a second arm configured to engage the second curved cutout.

13. The intervertebral prosthetic disc of claim 12, wherein the first and second cutouts are configured to engage the first arm and the second arm coupled at a pivot point.

14. The intervertebral prosthetic disc of claim 11, wherein the first and second bore holes are threaded.

15. The intervertebral prosthetic disc of claim 14, wherein the first and second cutout are configured to receive the second retaining feature in the form of a threaded holder.

16. The intervertebral prosthetic disc of claim 11, further comprising a core element at least partially disposed between the first and second endplates.

17. The intervertebral prosthetic disc of claim 16, wherein the core element comprises a first contoured surface in communication with and substantially corresponding to a surface of the first endplate, and a second contoured surface substantially in communication with and substantially corresponding to a surface-of the second endplate.

18. The intervertebral prosthetic disc of claim 17, wherein an articulating surface of the second endplate permits rotation of the second endplate relative to the core element substantially in the sagittal plane.

19. The intervertebral prosthetic disc of claim 17, wherein an articulating surface of the first endplate permits rotation of the first endplate relative to the core element substantially in all planes.

20. The intervertebral prosthetic disc of claim 11, wherein the first and second endplates are constrained to prevent separation of the first and second endplates from each other.

* * * * *